United States Patent
Mueller et al.

(10) Patent No.: US 11,506,875 B2
(45) Date of Patent: Nov. 22, 2022

(54) SURGICAL MICROSCOPE WITH AT LEAST ONE BEAM PATH SWITCHING DEVICE

(71) Applicant: Carl Zeiss Meditec AG, Jena (DE)

(72) Inventors: Andre Mueller, Koenigsbronn-Zang (DE); Daniel Kolster, Oberkochen (DE); Christian Beder, Aalen (DE); Thorsten Tritschler, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 383 days.

(21) Appl. No.: 16/590,030

(22) Filed: Oct. 1, 2019

(65) Prior Publication Data

US 2020/0033575 A1 Jan. 30, 2020

Related U.S. Application Data

(63) Continuation of application No. PCT/EP2018/062826, filed on May 16, 2018.

(30) Foreign Application Priority Data

May 17, 2017 (DE) .......................... 102017110779.7

(51) Int. Cl.
G02B 21/00 (2006.01)
G02B 27/10 (2006.01)
(Continued)

(52) U.S. Cl.
CPC ......... G02B 21/0012 (2013.01); G02B 21/02 (2013.01); G02B 21/22 (2013.01);
(Continued)

(58) Field of Classification Search
CPC ................ G02B 21/00; G02B 21/0012; G02B 21/0032; G02B 21/02; G02B 21/22;
(Continued)

(56) References Cited

U.S. PATENT DOCUMENTS 4,786,154 A * 11/1988 Fantone ............. G02B 21/0012
348/25
5,657,128 A 8/1997 Mueller et al.
(Continued)

FOREIGN PATENT DOCUMENTS

DE 102007019335 B3 9/2008
DE 102014201571 A1 7/2015
(Continued)

OTHER PUBLICATIONS

English translation of the International Preliminary Report on Patentability of the international searching authority dated Nov. 28, 2019 in international patent application PCT/EP2018/062826 on which the claim of priority is based.
(Continued)

*Primary Examiner* — Thong Q Nguyen
(74) *Attorney, Agent, or Firm* — Walter Ottesen, P.A.

(57) ABSTRACT

A surgical microscope for generating an image of an object region includes an eyepiece and an objective conjointly defining a viewing beam path, an image capturing device and a beam path switching device for out-coupling image information. The switching device is switchable between a first switching state wherein light in the viewing beam path is split into a first component along a first beam path to the eyepiece at an intensity IT1 and a second component along a second beam path to the image capturing device at an intensity IT2 and a second switching state wherein the light in the viewing beam path is deflected into the second beam path to the image capturing device at an intensity IU. The switching device includes a beam splitter movable in and out of the viewing beam path and a deflecting element movable into and out of the viewing beam path.

22 Claims, 31 Drawing Sheets

(51) Int. Cl.
*G02B 21/02* (2006.01)
*G02B 21/22* (2006.01)
*G02B 21/36* (2006.01)
*G02B 25/00* (2006.01)

(52) U.S. Cl.
CPC ......... *G02B 21/361* (2013.01); *G02B 25/001* (2013.01); *G02B 27/10* (2013.01)

(58) Field of Classification Search
CPC ...... G02B 21/361; G02B 27/10; G02B 27/00; G02B 27/09; G02B 27/0905; G02B 27/1006; G02B 27/106; G02B 27/126; G02B 27/14; G02B 27/141; G02B 27/145; G02B 27/283
USPC .................................. 359/368–390, 618–640
See application file for complete search history.

(56) References Cited

U.S. PATENT DOCUMENTS

| | | | |
|---|---|---|---|
| 5,697,368 A | 12/1997 | Luber et al. | |
| 5,867,309 A | 2/1999 | Spink et al. | |
| 6,661,572 B2 * | 12/2003 | Spink | G02B 21/0012 359/372 |
| 6,844,964 B2 * | 1/2005 | Muentener | G02B 21/22 359/363 |
| 6,999,649 B1 | 2/2006 | Chen et al. | |
| 7,505,199 B2 * | 3/2009 | Ito | G02B 21/20 359/363 |
| 8,018,651 B2 | 9/2011 | Sander | |
| 8,390,682 B2 * | 3/2013 | Minamide | G02B 21/18 348/80 |
| 8,427,743 B2 | 4/2013 | Sander | |
| 10,295,815 B2 | 5/2019 | Romanowski et al. | |
| 2015/0209116 A1 | 7/2015 | Jess et al. | |
| 2016/0091702 A1 | 3/2016 | Hauger | |
| 2016/0170194 A1 | 6/2016 | Mueller et al. | |
| 2016/0357003 A1 | 12/2016 | Hauger et al. | |

FOREIGN PATENT DOCUMENTS

| | | |
|---|---|---|
| DE | 102014210150 A1 | 12/2015 |
| WO | 2015124699 A2 | 8/2015 |
| WO | 2016130424 A1 | 8/2016 |

OTHER PUBLICATIONS

International Search Report dated Sep. 11, 2018 of international application PCT/EP2018/062826 on which this application is based.

* cited by examiner

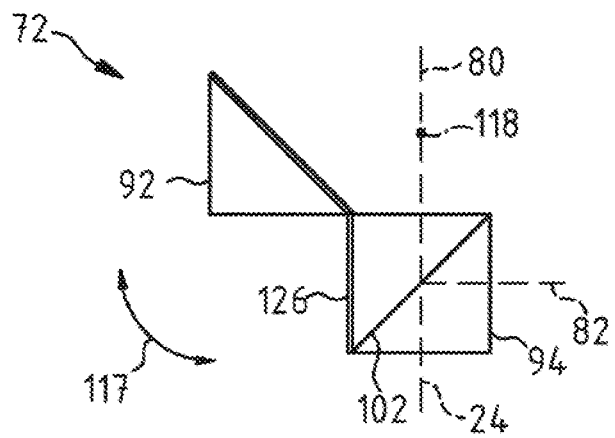
Fig. 12C
Fig. 12D
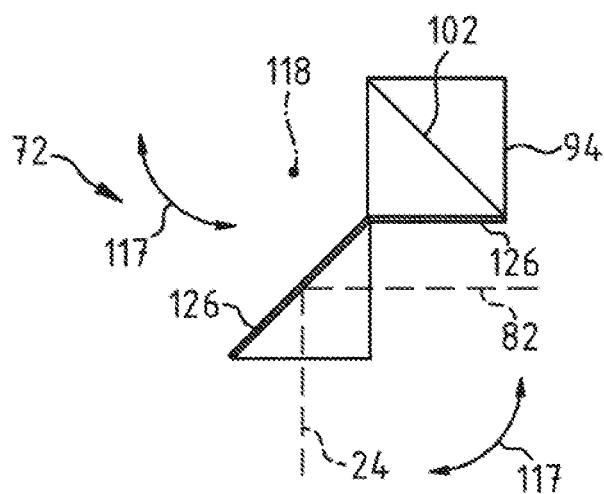

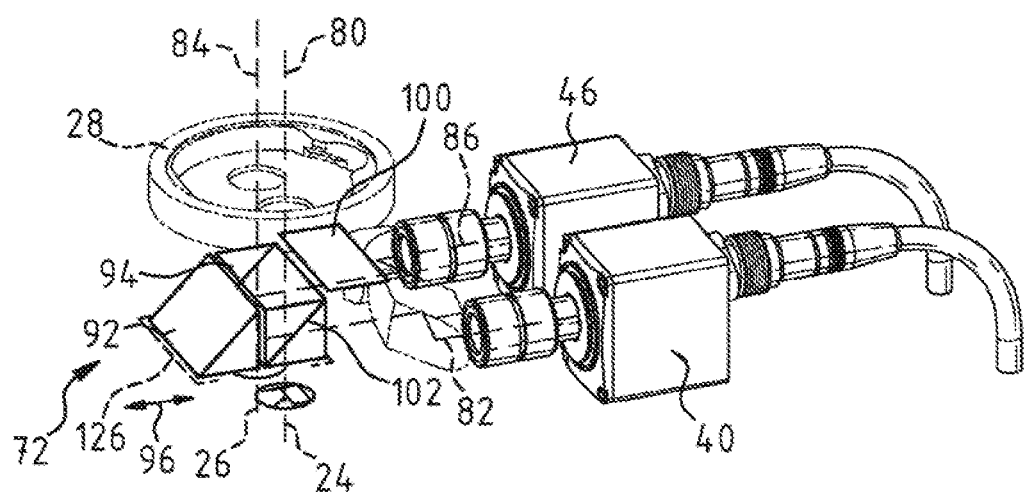
Fig. 14A
Fig. 14B
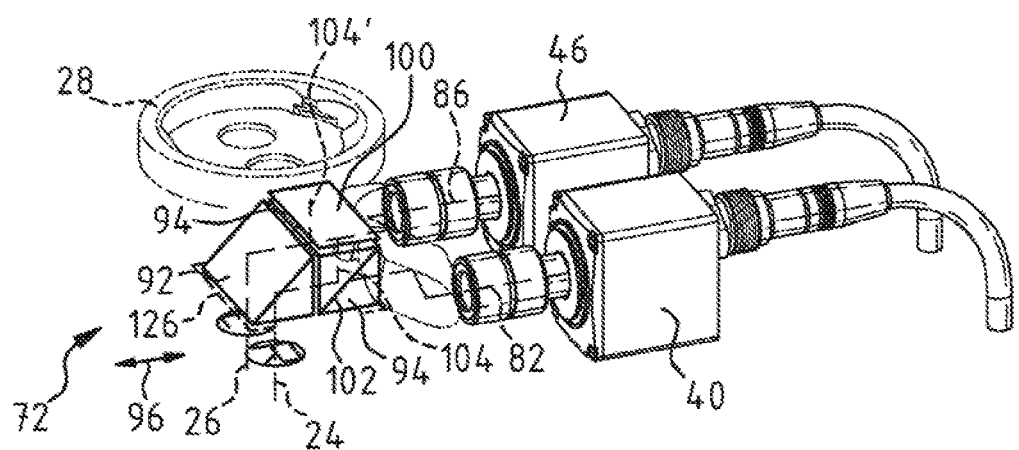

Fig. 15A
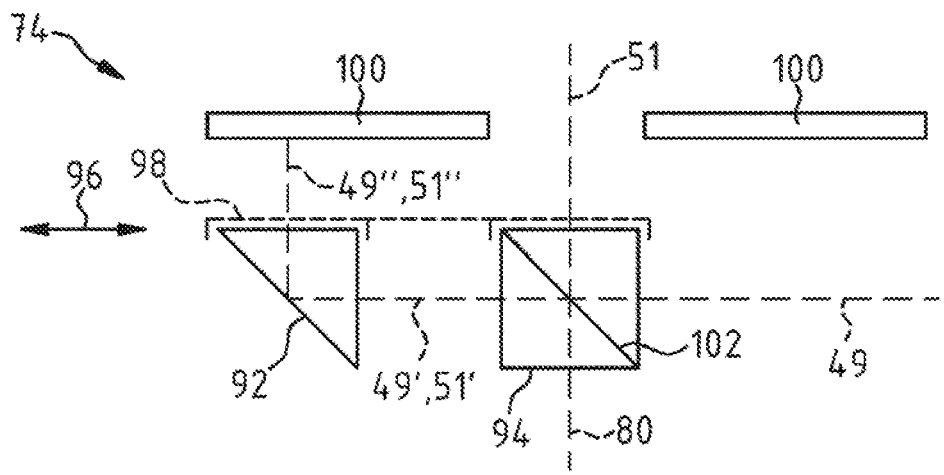
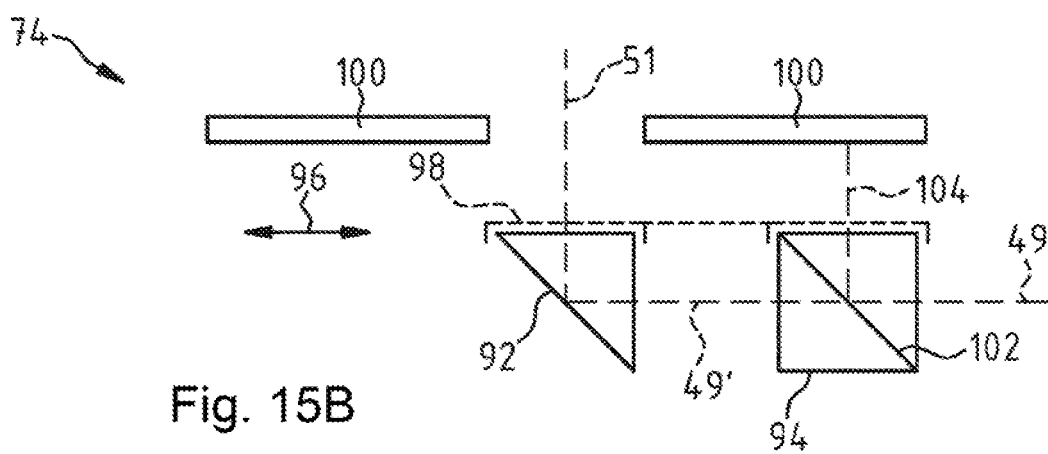
Fig. 15B
Fig. 15C
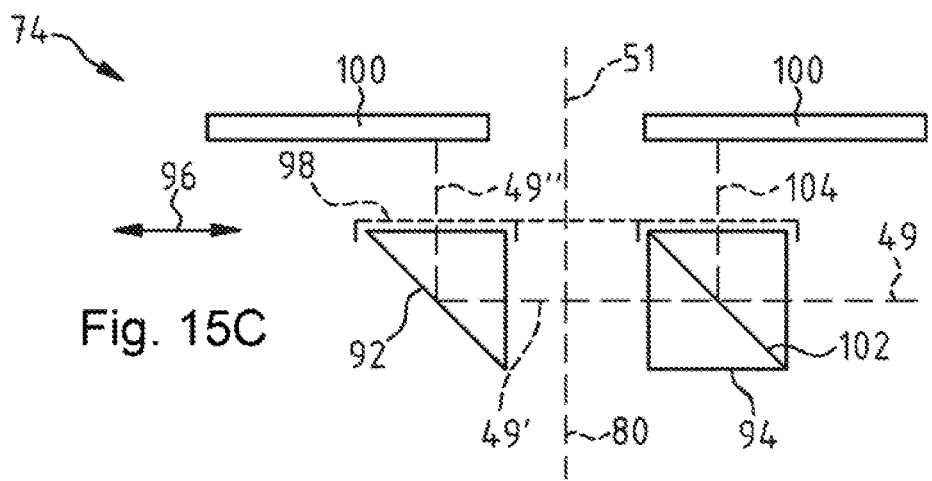

Fig. 19A
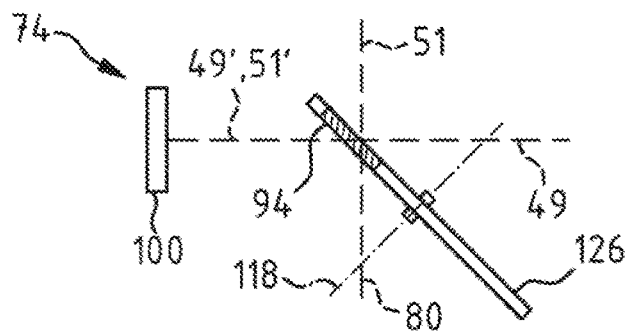
Fig. 19B
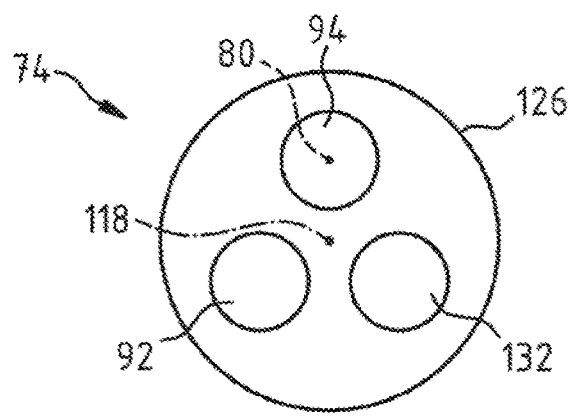
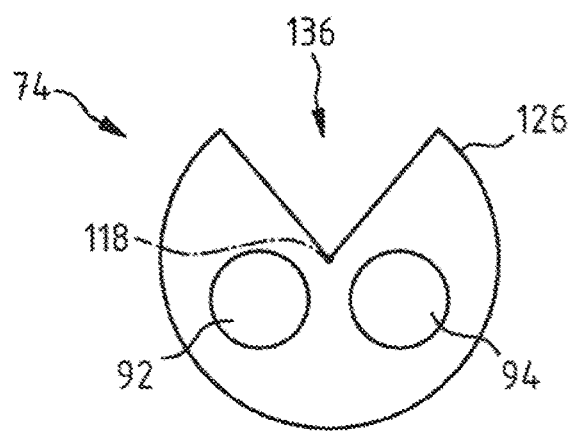
Fig. 20

SURGICAL MICROSCOPE WITH AT LEAST ONE BEAM PATH SWITCHING DEVICE

CROSS REFERENCE TO RELATED APPLICATIONS

This application is a continuation application of international patent application PCT/EP2018/062826, filed May 16, 2018, designating the United States and claiming priority from German application 10 2017 110 779.7, filed May 17, 2017, and the entire content of both applications is incorporated herein by reference.

FIELD OF THE INVENTION

The invention relates to a surgical microscope for producing an observation image of an object region having an observation beam path that extends through a main objective system.

BACKGROUND OF THE INVENTION

Surgical microscopes are used in various medical disciplines, such as neurosurgery, minimally invasive surgery and ophthalmology, for example. In particular, they serve to allow an operating physician to view an operating region with magnification.

US 2016/0357003 describes a surgical microscope having an eyepiece in which image data displayed on a display can be shown to an observer in superposition with the image of the object region. To this end, the surgical microscope contains a beam splitter arranged in the optical observation beam path. This beam splitter reflects an image of the object region displayed by way of a display into the optical observation beam path, the image being captured by way of an image sensor of an image capturing device in a characteristic wavelength range. Observation light from the optical observation beam path is guided here to the image sensor.

U.S. Pat. Nos. 8,018,651 and 8,427,743 disclose a surgical microscope for producing an observation image of an object region, containing a beam path switching device, arranged in the observation beam path, for coupling out image information. The beam path switching device serves to split light that is guided in the observation beam path in a first switching state among a first beam path and a second beam path, wherein the first beam path is guided to an eyepiece and the second beam path is guided to an image capturing device. In a second switching state, the beam path switching device can deflect the light that is guided in the observation beam path with the intensity IU into the second beam path.

SUMMARY OF THE INVENTION

It is an object of the invention to provide a surgical microscope having an image capturing device for capturing digital images of the object region in which the image of the object region can be displayed to an observer in an eyepiece and in which the amount of the light that is guided from the observation or viewing beam path to the image capturing device is settable.

Firstly, the surgical microscope of the invention is based on the finding that the visualization of an object region in an eyepiece with an optical observation beam path in a surgical microscope offers the advantage that a surgeon can observe an operating region both with a good optical imaging quality and a natural visual impression with color fidelity, even in the case of a high magnification. Secondly, the invention is based on the finding that the digital capture and display of object structures in an operating region is advantageous in numerous applications of surgical microscopes. This is because, firstly, comparatively little illumination light is required for the digital capture and display of object structures in an operating region, which means that the radiation exposure of body tissue is reduced. In addition, the digital capture and display of object structures in an operating region allows tissue structures which cannot even be captured in the spectral ranges of visible light to be displayed for an observer. Moreover, the digital capture and the display of object structures in an operating region makes it possible for them to be easily visualized to a plurality of persons at the same time. Not only does this facilitate the assistant in surgical operations, it also offers an excellent way of teaching in particular operation techniques with a surgical microscope.

The invention is also based on the finding that the visualization of data that were digitally captured using an image capturing device and subsequently prepared in a computer unit may simplify the orientation in an operating region for a surgeon and may also improve the handling of a surgical microscope.

A surgical microscope according to the invention for producing an observation image of an object region has an observation or viewing beam path that extends through a main objective system. Such a surgical microscope contains a beam path switching device for coupling out image information that splits light that is guided in the observation beam path in a first switching state among a first beam path with light of the intensity IT1 and a second beam path with light of the intensity IT2, wherein the first beam path is guided to an eyepiece and the second beam path is guided to an image capturing device, and which deflects the light that is guided in the observation beam path with the intensity IU into the second beam path in a second switching state. For the ratio Q of the intensity IT2 of the light that is guided into the second beam path in the first switching state of the beam path switching device and the intensity IU of the light that is deflected into the second beam path in the second switching state of the switching device, the following preferably applies: $Q:=IT2/IU \approx 25\%$.

It is advantageous if the beam path switching device transfers light of the intensity IB that is guided in the observation beam path in a third switching state into the first beam path as light of the intensity IB, that is, without intensity loss.

It is advantageous in particular if the surgical microscope has a beam path switching device for coupling in image information that superposes an image displayed on a display device onto the first beam path in a first switching state and that guides the image displayed on the display device to the eyepiece without light from the first beam path in a second switching state. In this way it is possible to visualize for an observer display information in the eyepiece without this being adversely affected by light entering the eyepiece from the object region.

It is in particular an idea of the invention to maximize in each case the light quantity for the observation of the object region with an optical observation beam path using the surgical microscope in different operating states such that a maximum light quantity can be guided to the eyes of an observer from the object region.

A surgical microscope according to the invention can have a computational unit, connected to an image processing and control device, for providing object region image data that are obtained in an imaging method and are able to be supplied by the display device and have a switchable imaging optical unit that, in a first switching state, supplies to an eyepiece using an optical observation beam path the observation image of the object region on which the object region image data, which are displayed with the display device, are able to be superposed in a spatially correct manner and that, in a further switching state that differs from the first switching state, interrupts the optical observation beam path from the object region to the eyepiece to display in the eyepiece an image of the object region that is captured with the image capturing device and is displayed with the display device from the optical observation beam path.

Object region image data obtained using an imaging method are understood to be information in the form of images of the object region that are obtained preferably preoperatively for example using magnetic resonance imaging (NMR), positron emission tomography (PET), magnetoencephalography (MEG) or single-photon emission computed tomography (SPECT). Such object region image data can be in particular angiography data, magnetic resonance imaging data, X-ray tomography data or spatially resolved image data captured using an endoscope, laparoscope or microscope. In particular, object region image data obtained using an imaging method can be three-dimensional image data. In principle, the object region image data can also be intraoperatively obtained image data.

A surgical microscope according to the invention can have a device for referencing a coordinate system that is spatially fixed in relation to the surgical microscope to a coordinate system of the object region and to a coordinate system of object region image data obtained in an imaging method. Such a device for a surgical microscope is described for example in U.S. Pat. No. 5,657,128, to which reference is made herewith and the disclosure of which is incorporated into the disclosure of this application. That device makes it possible that in the surgical microscope of the invention the object region image data are able to be superposed in a spatially correct manner on the observation image of the object region in the surgical microscope using the display device.

For this spatially correct superposition it is necessary for the coordinate system of the object region image data to be referenced to or correlated with the coordinate system of the surgical microscope and a coordinate system of the object region that is observed with the surgical microscope. Such referencing or correlating of the coordinate systems is described for example in U.S. Pat. No. 5,697,368, to which reference is made herewith and the disclosure of which is incorporated into the disclosure of this application. Correlating or referencing corresponding coordinate systems makes it possible that the coordinates of the object region image data in the coordinate system of the image data can be converted into the coordinate system of the surgical microscope such that the image data are visualized with the image of the object region for an observer, such that mutually corresponding structures in the object region image data and the image of the object region are located on top of one another.

BRIEF DESCRIPTION OF THE DRAWINGS

The invention will now be described with reference to the drawings wherein:

FIG. 12C and FIG. 12D show a further beam path switching device for use in a surgical microscope for stereoscopically visualizing an object region, with which two different switching states are settable;

FIG. 14A and FIG. 14B and FIG. 14C and FIG. 14D show two further beam path switching devices for use in a surgical microscope for stereoscopically visualizing an object region, with which in each case two different switching states are settable;

FIG. 15A and FIG. 15B and FIG. 15C show a further beam path switching device in a surgical microscope for stereoscopically visualizing an object region in different switching states;

FIG. 19A and FIG. 19B show different views of a further beam path switching device for use in a surgical microscope for stereoscopically visualizing an object region;

FIG. 20 shows a further beam path switching device for use in a surgical microscope for stereoscopically visualizing an object region;

DESCRIPTION OF THE PREFERRED EMBODIMENTS OF THE INVENTION

Figure 1:
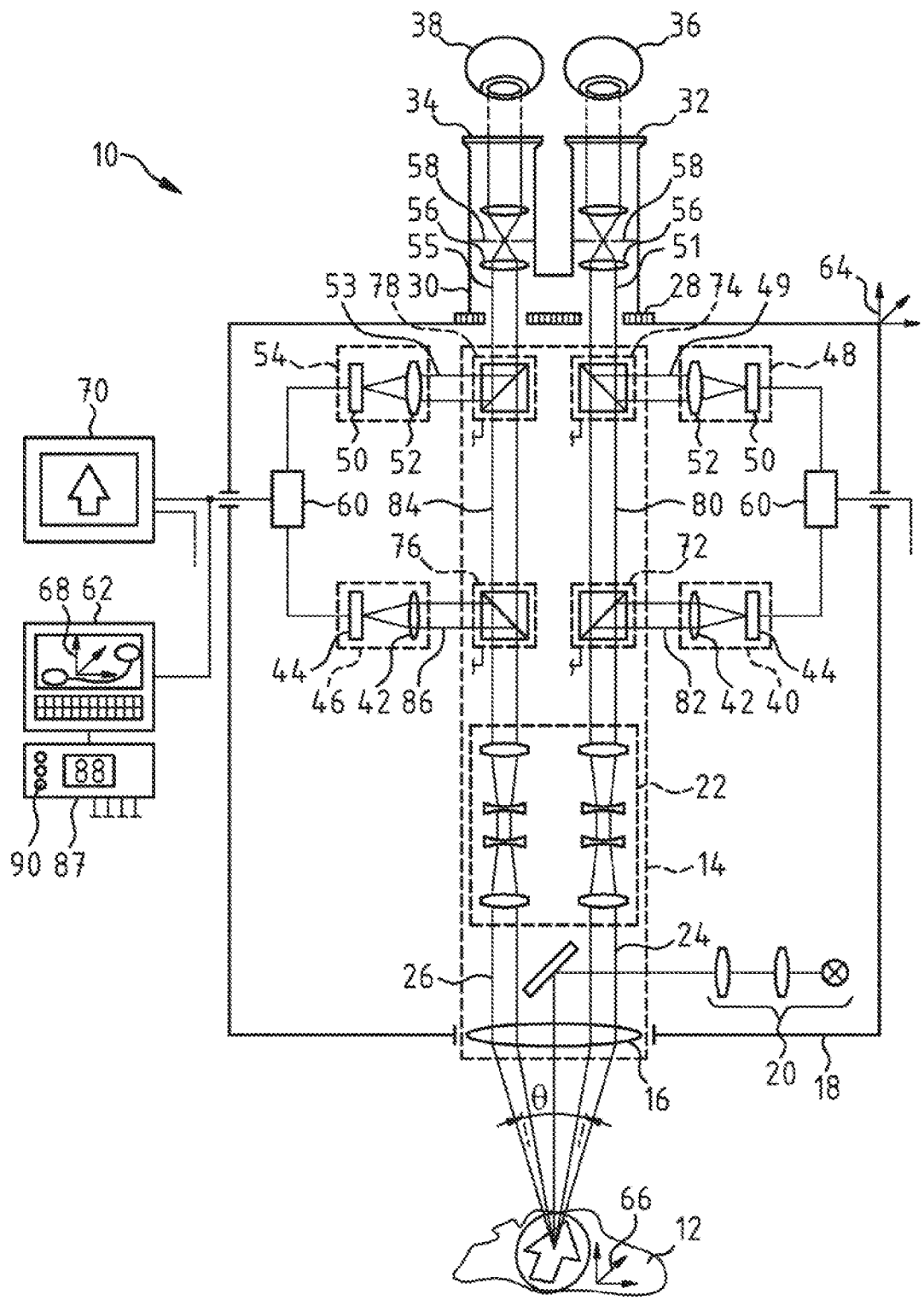
FIG. 1 shows a surgical microscope for stereoscopically visualizing an object region with a binocular tube in a first operating state.

The surgical microscope 10 shown in FIG. 1 serves for the stereoscopic observation of an object region 12. It has an imaging optical unit 14 with a microscope main objective system 16, the imaging optical unit being held in a main body 18. The surgical microscope 10 contains an illumination device 20 for illuminating the object region 12 through the microscope main objective system 16. It has an afocal magnification system 22, through which a first stereoscopic partial observation beam path 24 and a second stereoscopic partial observation beam path 26 are guided. The surgical microscope 10 has a binocular tube 30 connected to an interface 28 of the main body 18, the binocular tube having a first eyepiece 32 and a second eyepiece 34 for a right and a left eye 36, 38 of an observer. The microscope main objective system 16 in the surgical microscope 10 is traversed by the first stereoscopic partial observation beam path 24 and the second stereoscopic partial observation beam path 26.

In the surgical microscope 10, there is a first image capturing device 40 with an objective lens system 42 and with an image sensor 44. The image capturing device 40 serves to capture image information from the first stereoscopic partial observation beam path 24. By means of a second image capturing device 46, image information from the second stereoscopic partial observation beam path 26 can be captured in the surgical microscope 10. The second image capturing device 46 likewise has an objective lens system 42 and contains an image sensor 44.

For visualizing display information in the first eyepiece 32, the surgical microscope 10 contains a first display device 48 with a display 50 and a display lens 52. Display information of a display 50 can be displayed with a second display device 54 in the second eyepiece 34 in the surgical microscope 10. The second display device 54 likewise contains a display lens 52. The display 50 of the first and second display device 48, 54 is configured in the form of a digital mirror display (DMD). It thus makes fast changing of images that are displayed therewith possible. It should be noted, however, that the display 50 of the first and second display device 48, 54 may also be an LCD display or an OLED display.

The binocular tube 30 contains tube lenses 56 which transfer the light from the first or second stereoscopic partial observation beam path 24, 26 and/or the display information of the displays 50 into an intermediate image that is arranged in the intermediate image plane 58.

There is in each case one image processing and control device 60, which is assigned to the displays 50 and connected to a computational unit 62, for actuating the displays 50 in the surgical microscope 10.

The computational unit 62 serves for providing spatially resolved three-dimensional object region image data that are supplied to the first display device 48 and the second display device 54 for display and that are obtained for example preoperatively in an imaging method for example using magnetic resonance imaging or X-ray tomography.

In this case, the computational unit 62 provides the three-dimensional object region image data as image data that are referenced to the coordinate system of the object region 12 and the coordinate system of the surgical microscope 10. To this end, the computational unit 62 contains a computer program that references a coordinate system 64 that is locationally fixed relative to the surgical microscope 10 to a coordinate system 66 that is locationally fixed with respect to the object region 12 and to a coordinate system 68 of the object region image data from a piece of position information relating to the surgical microscope 10 and a piece of position information relating to the object region 12.

The three-dimensional object region image data are visualized here with a stereoscopic, three-dimensional visual impression for an observer looking into the binocular tube 30 of the surgical microscope 10.

It should be noted that in a modified embodiment of the inventors, the computational unit 62 can be configured for providing two-dimensional object region image data so as to display therewith an image of the object region for example only in a single stereoscopic partial observation beam path of the surgical microscope.

In order to visualize images of the object region 12 that are captured from the first and second stereoscopic partial observation beam path 24, 26 by way of the image capturing devices 40, 46 outside the binocular tube 30, the surgical microscope 10 additionally has an image reproducing device 70, preferably configured as a 3D monitor, for three-dimensional visualization of the object region 12, the image reproducing device being combined with the image processing and control devices 60 that are assigned to the displays 50. It is possible using the image reproducing device 70 for the object region 12 to be displayed here not only to the observer but also to further persons in an operating theater with a stereoscopic visual impression.

The imaging optical unit 14 contains four beam path switching devices 72, 74, 76, 78, for which in each case three different switching states are settable. The beam path switching devices 72, 74 serve for switching a beam path to the first image capturing device 40 and to the first eyepiece 32. It is the object of the beam path switching devices 76, 78 to switch a beam path to the second image capturing device 46 and to the second eyepiece 34.

It should be noted that the surgical microscope 10 in one modified embodiment may, however, also be configured for setting only two different switching states of beam path switching devices, which are arranged in a beam path of the surgical microscope 10 or in a plurality of beam paths of the surgical microscope 10.

FIG. 1, FIG. 2, FIG. 3 and FIG. 4 show the surgical microscope 10 in different operating states in which the settings of the beam path switching devices 72, 74, 76 and 78 differ.

Figure 2:
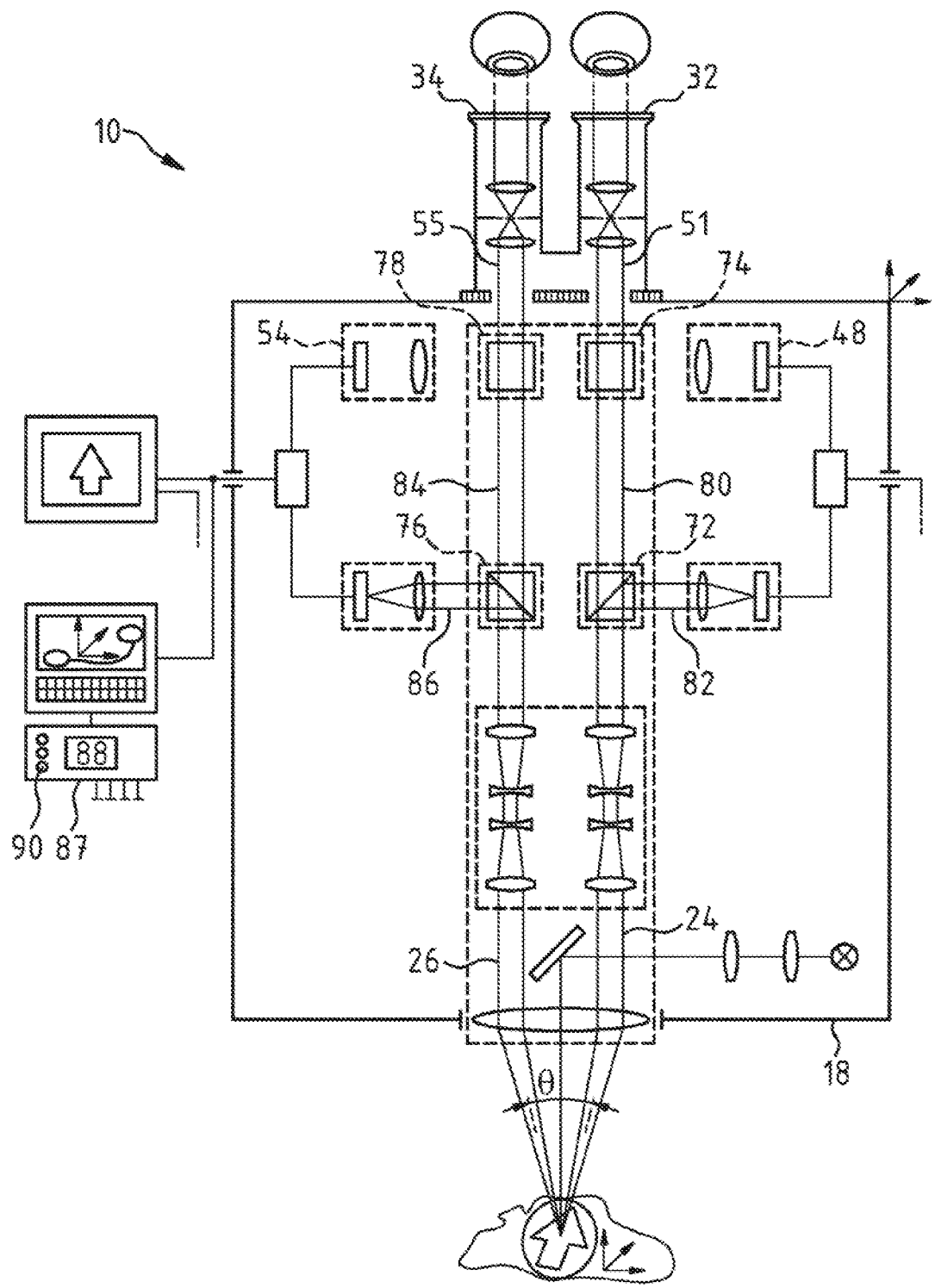
FIG. 2 shows the surgical microscope in a second operating state.

In the first switching state of the beam path switching device 72 shown in FIG. 1 and FIG. 2, the beam path switching device 72 splits the light that is guided in the observation beam path 24 among a first beam path 80 and a second beam path 82. The first beam path 80 is guided to the first eyepiece 32 in the surgical microscope 10. The second beam path 82 leads to the first image capturing device 40 in the surgical microscope 10.

Figure 3:
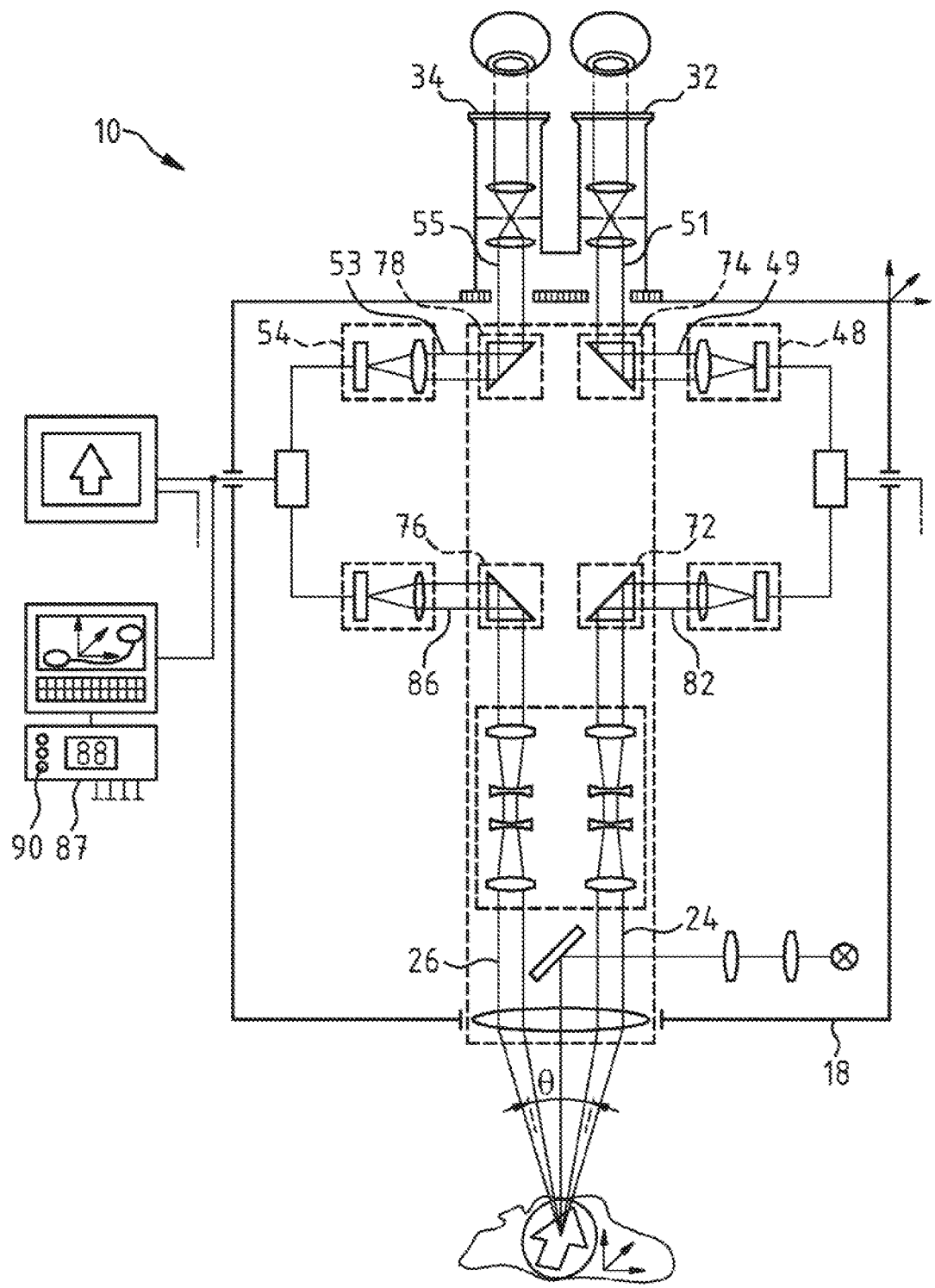
FIG. 3 shows the surgical microscope in a third operating state.

By contrast, the light that is guided in the stereoscopic partial observation beam path 24 is deflected entirely into the second beam path 82 by way of the beam path switching device 72 that is in a second switching state shown in FIG. 3.

Figure 4:
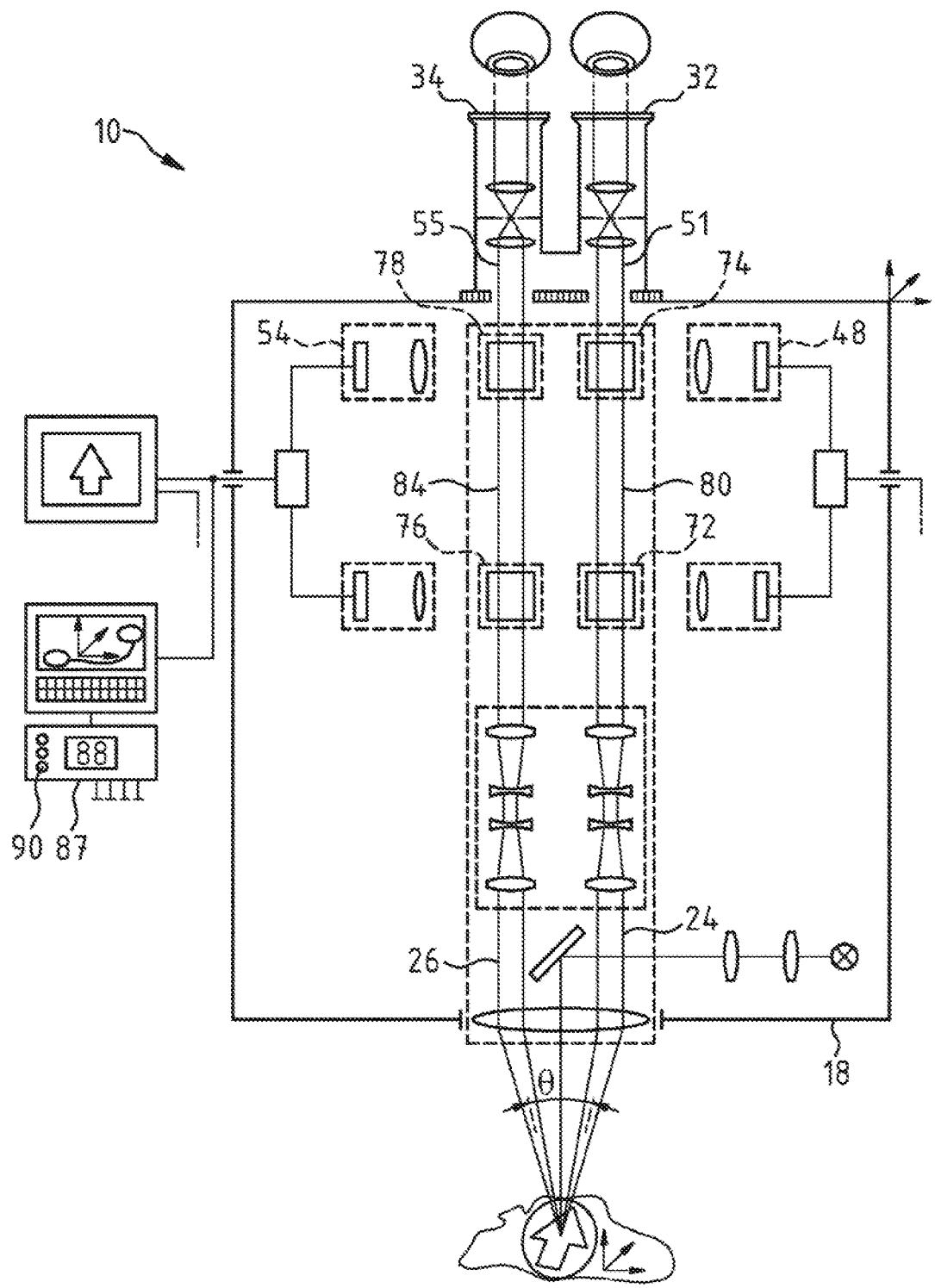
FIG. 4 shows the surgical microscope in a fourth operating state.

In a third switching state shown in FIG. 4, the beam path switching device 72 releases the first stereoscopic partial observation beam path 24. The light that is guided in the first stereoscopic partial observation beam path 24 is then guided in its entirety in the first beam path 80 to the first eyepiece 32.

For the ratio Q of the intensity IT2 of the light that is guided into the second beam path 82 in the first switching state of the beam path switching device 72 and the intensity IU of the light that is deflected into the second beam path 82 in the second switching state by way of the beam path switching device 72, the following applies, for example: $Q=IT2/IU \approx 25\%$.

The switching state of the beam path switching device 76 shown in FIG. 1 to FIG. 4 in each case corresponds to the switching state of the beam path switching device 72. In the switching state shown in FIG. 1 and FIG. 2, the beam path switching device 76 splits the light that is guided in the second stereoscopic partial observation beam path 26 among a further first beam path 84 and a further second beam path 86. The further first beam path 84 is guided to the second eyepiece 34 in the surgical microscope 10. The further second beam path 86 there leads to the second image capturing device 46 in the surgical microscope 10.

By contrast, the light that is guided in the stereoscopic partial observation beam path 26 is deflected entirely into the further second beam path 86 by way of the beam path switching device 76 that is in a second switching state shown in FIG. 3.

In a third switching state shown in FIG. 4, the beam path switching device 76 releases the stereoscopic partial observation beam path 26. The light that is guided in the second stereoscopic partial observation beam path 26 is then guided in its entirety to the second eyepiece 34.

For the ratio Q of the intensity IT2 of the light that is guided into the further second beam path 86 in the first switching state of the beam path switching device 76 and the intensity IU of the light that is deflected into the further second beam path 86 in the further second switching state by way of the beam path switching device 76, again the following applies here, for example: $Q=IT2/IU \approx 25\%$.

In the first switching state of the beam path switching device 74, shown in FIG. 1, the beam path switching device 74 superposes a display beam path 49 with the image information displayed on the first display device 48 on the first beam path 80. In the second switching state of the beam path switching device 74, shown in FIG. 3, the display beam path 49 with the image information displayed on the display device 48 is deflected into the beam path 51 to the first eyepiece 32. In this case, no light is guided from the first beam path 80 to the eyepiece 32.

For the ratio Q of the intensity IT2 of the light of the display device 48 that is guided from the first beam path 80 into the beam path 51 to the first eyepiece 32 in the first switching state of the beam path switching device 74 and the intensity IU of the light of the display device that is deflected into the beam path 51 to the eyepiece 32 in the second switching state of the beam path switching device 74, the following applies, for example: $Q=IT2/IU \approx 25\%$.

In a third switching state shown in FIG. 2 and in FIG. 4, the beam path switching device 74 releases the first beam path 80. The light that is guided in the first beam path 80 is then guided in its entirety in the beam path 51 to the first eyepiece 32.

The switching state of the beam path switching device 78 shown in FIG. 1 to FIG. 4 in each case likewise corresponds to the switching state of the beam path switching device 74. In the first switching state of the beam path switching device 74, shown in FIG. 1, the beam path switching device 78 superposes the image information provided by the second display device 54 in a second display beam path 53 on the further first beam path 84. In the second switching state of the beam path switching device 78, shown in FIG. 3, the display beam path 53 with the image information displayed on the display device 54 is deflected into the beam path 55 to the second eyepiece 34. In this case, no light is guided from the further first beam path 84 to the eyepiece 34.

In a third switching state shown in FIG. 2 and in FIG. 4, the beam path switching device 78 releases the further first beam path 84. The light that is guided in the further first beam path 84 is then guided in its entirety into the beam path 55 to the second eyepiece 34.

For the ratio Q of the intensity IT2 of the light of the display device 54 that is guided from the further first beam path 84 into the beam path 55 to the second eyepiece 34 in the first switching state of the beam path switching device 78 and the intensity IU of the light of the display device that is deflected into the beam path 55 to the eyepiece 34 in the further second switching state of the beam path switching device 78, the following likewise applies here, for example: $Q=IT2/IU \approx 25\%$.

For controlling microscope functions, the surgical microscope 10 contains a control device 87 having a settable coupling device 88 that can be selectively activated and deactivated by an operator.

In the activated state, the coupling device 88 couples the beam path switching devices 72, 74, 76 and 78 for setting switching states that are coordinated with one another. The coupling device or coupling unit 88 functions to couple the first beam path switching device 72 and the second beam path switching device 76 to set mutually matched switching states. The activated coupling device 88 brings about the setting of the first or the third switching state of the beam path switching device 74 when the first switching state of the beam path switching device 72 is set, or brings about the setting of the first or the third switching state of the beam path switching device 72 when the first switching state of the beam path switching device 74 is set. Analogously, the coupling device 88 in the activated state is used to bring about the setting of the second switching state of the beam path switching device 74 when the second switching state of the first beam path switching device 72 is set, or to bring about the setting of the second switching state of the beam path switching device 72 when the second switching state of the beam path switching device 74 is set. The coupling device 88 in its activated state also brings about the setting of the first or the third switching state of the beam path switching device 74 when the third switching state of the beam path switching device 72 is set, or brings about the setting of the first or the third switching state of the beam path switching device 72 when the third switching state of the beam path switching device 74 is set.

The activated coupling device 88 moreover brings about the setting of the first or the third switching state of the beam path switching device 78 when the first switching state of the beam path switching device 76 is set, or brings about the setting of the first or the third switching state of the beam path switching device 76 when the first switching state of the beam path switching device 78 is set. Analogously, the coupling device 88 is then used to also set the second switching state of the beam path switching device 78 when the second switching state of the first beam path switching device 76 is set, or to set the second switching state of the beam path switching device 78 when the second switching state of the beam path switching device 76 is set. The coupling device 88 in its activated state also brings about the setting of the first or the third switching state of the beam path switching device 78 when the third switching state of the beam path switching device 76 is set, or brings about the setting of the first or the third switching state of the beam path switching device 76 when the third switching state of the beam path switching device 78 is set.

The activated coupling device 88 additionally brings about the setting of the first switching state of the beam path switching device 76 when the first switching state of the beam path switching device 72 is set, and brings about the setting of the second switching state of the beam path switching device 76 when the second switching state of the beam path switching device 72 is set, and also brings about the setting of the third switching state of the beam path switching device 76 when the third switching state of the beam path switching device 72 is set.

The activated coupling device 88 finally brings about the setting of the first switching state of the beam path switching device 72 when the first switching state of the beam path switching device 76 is set, and brings about the setting of the second switching state of the beam path switching device 72 when the second switching state of the beam path switching device 76 is set, and also brings about the setting of the third switching state of the beam path switching device 72 when the third switching state of the beam path switching device 76 is set.

If, on the other hand, the coupling device 88 is deactivated, an operator can set the switching states of the beam path switching devices 72, 74, 76 and 78 independently from one another on an input unit 90 of the control device 87.

It should be noted that in a modified embodiment of the surgical microscope 10, the coupling device 88 may upon activation bring about the setting of the first switching state of the beam path switching device 78 when the first switching state of the beam path switching device 74 is set, and bring about the setting of the second switching state of the beam path switching device 78 when the second switching state of the beam path switching device 74 is set, and bring about the setting of the third switching state of the beam path switching device 78 when the third switching state of the beam path switching device 74 is set. It should also be noted that in a further modified embodiment of the surgical microscope 10, the coupling device 88 may upon activation bring about the setting of the first switching state of the beam path switching device 74 when the first switching state of the beam path switching device 78 is set, and bring about the setting of the second switching state of the beam path switching device 74 when the second switching state of the beam path switching device 78 is set, and bring about the setting of the third switching state of the beam path switching device 74 when the third switching state of the beam path switching device 78 is set.

Figure 5A:
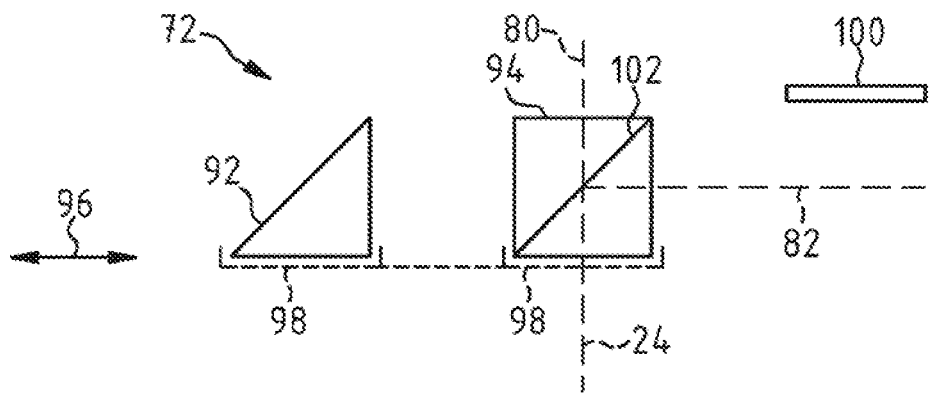
FIG. 5A and FIG. 5B and FIG. 5C show a beam path switching device in the surgical microscope in different switching states.
Figure 5B:
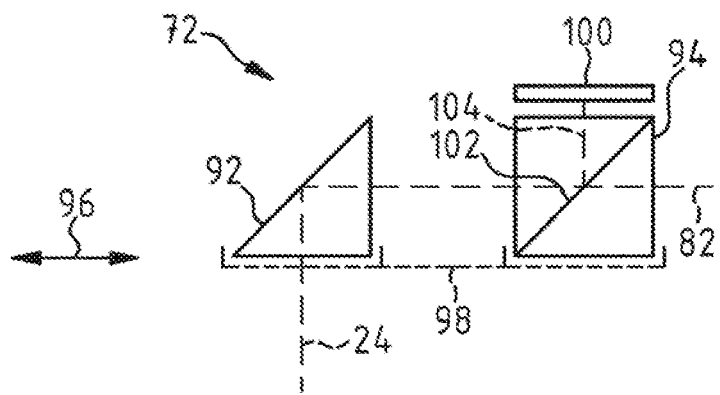
Figure 5C:
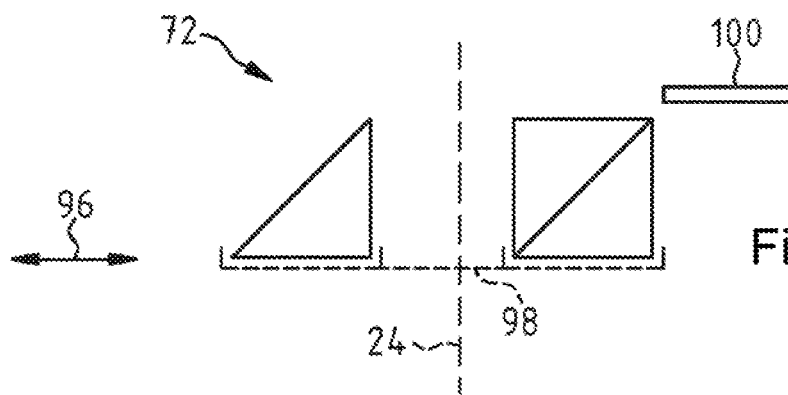

FIG. 5A and FIG. 5B and FIG. 5C show the beam path switching device 72 in the surgical microscope 10 in different switching states. The beam path switching device 72 has a deflection element 92 in the form of a deflection prism and contains a beam splitter element 94 in the form of a splitter cube. The deflection element 92 and the beam splitter element 94 are arranged on a carrier element 98 that is displaceable in the surgical microscope 10 in the direction of the double-headed arrow 96 preferably perpendicularly to the stereoscopic partial observation beam path 24. It should be noted that in a modified embodiment, the deflection element 92 and the beam splitter element 94 that are arranged in a surgical microscope 10 in a plane that is skewed in relation to the partial observation beam path 24 such that they are displaceable relative to the stereoscopic partial observation beam path 24 may be held on the carrier element 98. For setting the different switching states of the beam path switching device 72, the carrier element 98 with the deflection element 92 arranged thereon and the beam splitter element 94 is displaced in the direction of the double-headed arrow 96. The beam path switching device 72 has a light trap 100 that is arranged in a locationally fixed manner in the surgical microscope 10.

In the first switching state shown in FIG. 5A, the light is guided from the stereoscopic partial observation beam path 24 through the beam splitter element 94. This light is split at a splitter layer 102 of the beam splitter element 94 among the first beam path 80 and the second beam path 82.

By contrast, the beam path switching device 72 in the second switching state, shown in FIG. 5B, steers the light from the first stereoscopic partial observation beam path 24 through the beam splitter element 94 by way of the deflection element 92. The light from the first stereoscopic partial observation beam path 24 is then split among the second beam path 82 and a further beam path 104 at a splitter layer 102 in the beam splitter element 94. The further beam path 104 extends to the light trap 100 that receives the light from the beam path 104 with the result that the light that is guided in the further beam path 104 in the surgical microscope 10 does not produce stray light that disturbs the observation image or reflections that disturb the observation image.

In the third switching state shown in FIG. 5C, the beam path switching device 72 releases the stereoscopic partial beam path 24.

Figure 6A:
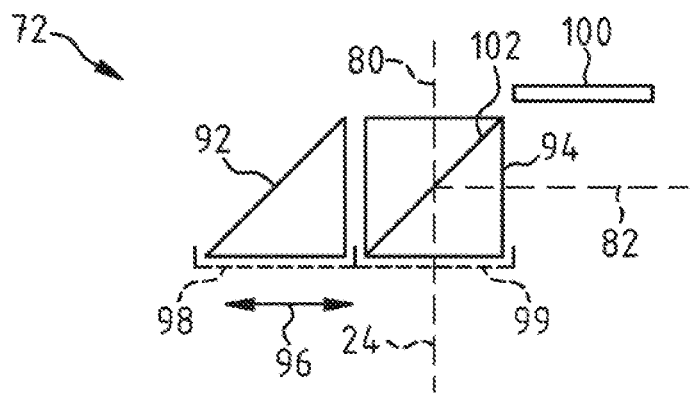
FIG. 6A and FIG. 6B and FIG. 6C show a further beam path switching device in different switching states for use in the surgical microscope.
Figure 6B:
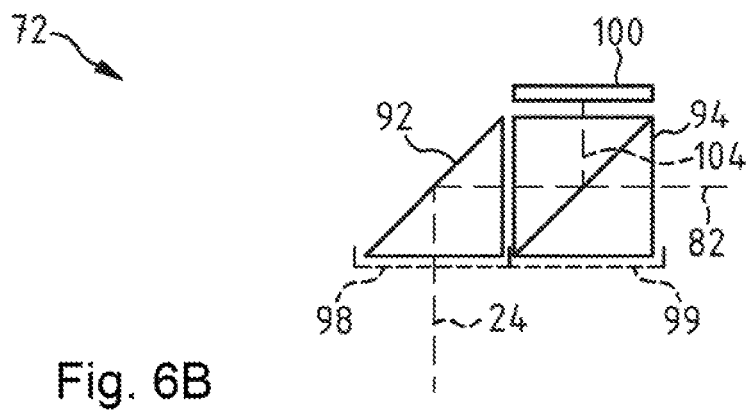
Figure 6C:
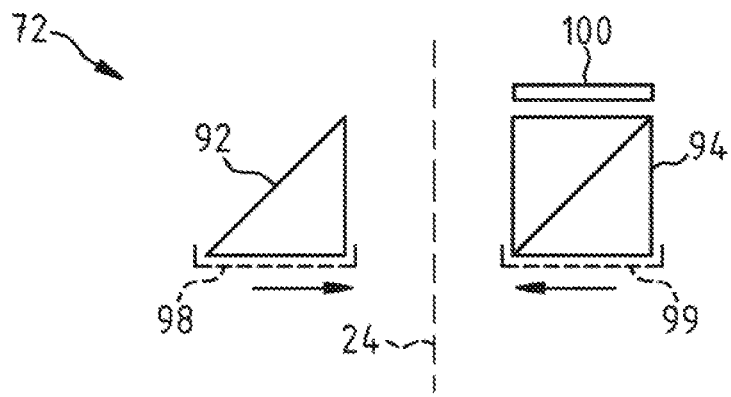

FIG. 6A and FIG. 6B and FIG. 6C show a further beam path switching device 72 in different switching states that is suitable for use in the surgical microscope 10 for switching the first stereoscopic partial observation beam path 24. The beam path switching device 72 also contains a deflection element 92 in the form of a deflection prism and has a beam splitter element 94, in the form of a splitter cube, with a splitter layer 102. The deflection element 92 and the beam splitter element 94 are held here on carrier elements 98, 99 that are arranged in a surgical microscope 10 so as to be displaceable relative to one another and relative to the stereoscopic partial observation beam path 24 in the direction of the double-headed arrow 96 preferably perpendicularly to the stereoscopic partial observation beam 24. It should be noted that in a modified embodiment, the deflection element 92 and the beam splitter element 94 that are arranged in a surgical microscope 10 in a plane that is skewed in relation to the partial observation beam path 24 such that they are displaceable relative to one another and relative to the stereoscopic partial observation beam path 24 may be held on carrier elements 98, 99. A light trap 100 that is arranged in a locationally fixed manner with respect to the stereoscopic partial observation beam path 24 is also present in the beam path switching device 72.

For setting the different switching states of the beam path switching device 72, the deflection element 92 that is secured on the carrier element 98 and the beam splitter element 94 that is secured on the carrier element 98 are each displaced in the direction of the double-headed arrow 96 with respect to the stereoscopic partial observation beam path 24.

In the first switching state, shown in FIG. 6A, the beam path switching device 72 splits the light from the first stereoscopic partial observation beam path 24 by way of the beam splitter element 94 at the splitter layer 102 among the first beam path 80 and the second beam path 82.

By contrast, the beam path switching device 72 in the second switching state, shown in FIG. 6B, is used to steer the light from the stereoscopic partial observation beam path 24 to the beam splitter element 94 by way of the deflection element 92. The light from the first stereoscopic partial observation beam path 24 that has been guided to the beam splitter element 94 is then split by way of the splitter layer 102 in the beam splitter element 94 among the second beam path 82 and a further beam path 104 that is perpendicular to the beam path 82. The further beam path 104 extends to the light trap 100 that receives the light from the beam path 104 with the result that the light that is guided in the further beam path 104 in the surgical microscope 10 does not produce stray light that disturbs the observation image or reflections that disturb the observation image.

In the switching state shown in FIG. 6C, the beam path switching device 72 releases the stereoscopic partial beam path 24.

Figure 7A:
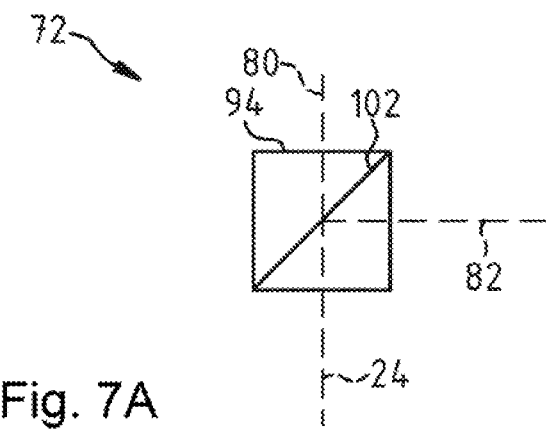
FIG. 7A and FIG. 7B and FIG. 7C show a further beam path switching device in different switching states for use in the surgical microscope.
Figure 7B:
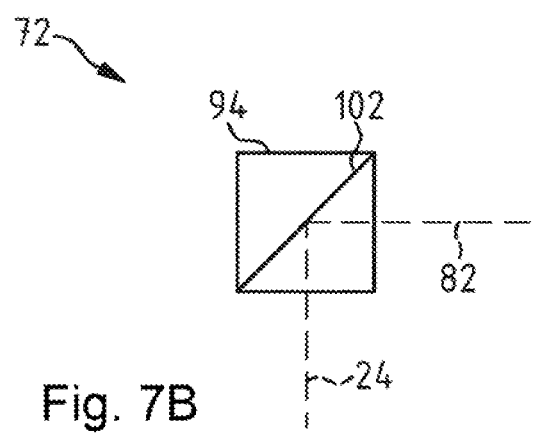
Figure 7C:
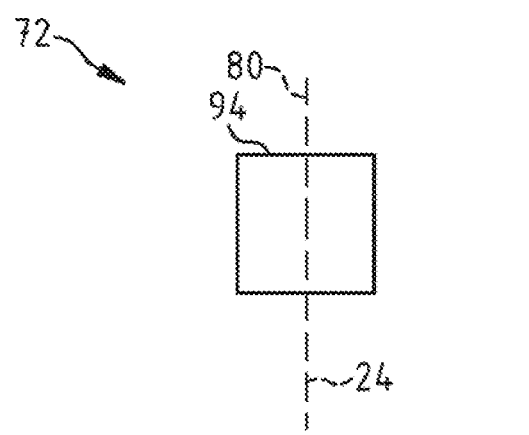

FIG. 7A and FIG. 7B and FIG. 7C show a further beam path switching device 72 in different switching states that is suitable for use in the surgical microscope 10.

The beam path switching device 72 contains a beam splitter element 94, in the form of a splitter cube, with an electrically controllable splitter layer 102. The splitter layer 102 can, for example, have a construction as described in U.S. Pat. No. 6,999,649 B1, to which reference is made herewith in the entirety thereof and the disclosure of which is incorporated into the description of this invention. In that case, the splitter layer 102 is embodied in the form of a layer having liquid crystals extending in a longitudinal direction, the orientation of which can be varied by setting a voltage and that reflect the light that is incident on the splitter layer 102 in dependence on the orientation of the liquid crystals.

In the first switching state shown in FIG. 7A, the splitter layer 102 in the beam splitter element 94 splits the light from the first stereoscopic partial observation beam path 24 among the first beam path 80 and the second beam path 82 with the split ratio Q, for example, Q=IT2/IU≈25%/100%.

By contrast, the beam path switching device 72 in the second switching state shown in FIG. 7B is used to split the light from the stereoscopic partial observation beam path 24 among the first beam path 80 and the second beam path 82 with the split ratio Q, for example, Q=IT2/IU≈0%/100%. In other words, the light is here deflected in its entirety from the stereoscopic partial observation beam path 24 into the second beam path 82.

In the third switching state shown in FIG. 7C, for the splitter layer 102 in the beam splitter element 94, the light is split from the stereoscopic partial observation beam path 24 among the first beam path 80 and the second beam path 82 with the split ratio Q, for example, Q=IT2/IU≈100%/0%. In this switching state, no light is therefore guided from the stereoscopic partial observation beam path 24 to the image capturing device 40 in the surgical microscope 10. In other words, the beam path switching device 72 in this switching state releases the stereoscopic partial observation beam path 24.

Figure 8A:
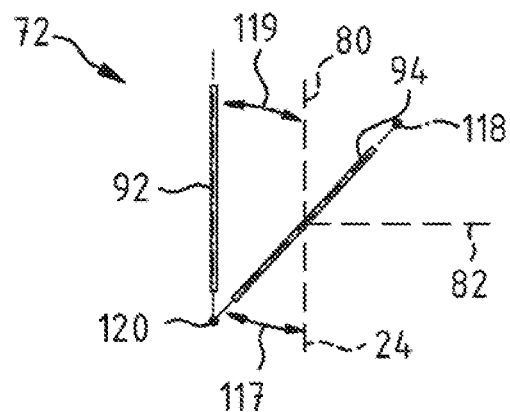
FIG. 8A and FIG. 8B and FIG. 8C show a further beam path switching device in different switching states for use in the surgical microscope.
Figure 8B:
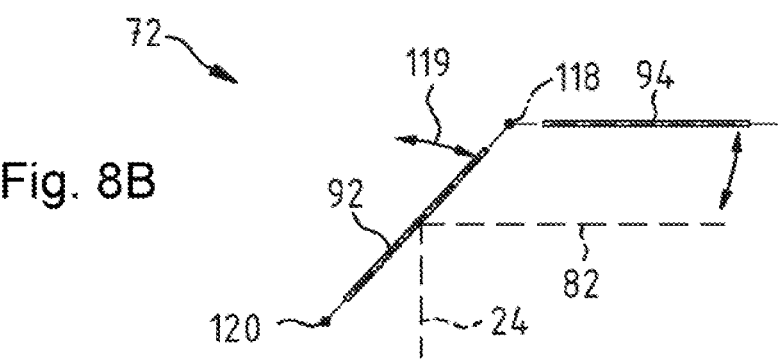
Figure 8C:
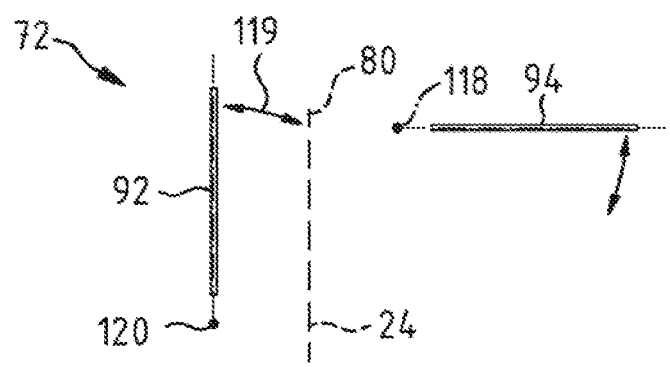

FIG. 8A and FIG. 8B and FIG. 8C show a further beam path switching device 72 in different switching states that is suitable for use in the surgical microscope 10. The beam path switching device 72 contains a beam splitter element 94, in the form of a splitter plate, and a deflection element 92 in the form of a folding mirror. The beam splitter element 94 in the beam path switching device 72 can here be pivoted about an axis of rotation 118 in accordance with the double-headed arrow 117. By contrast, the deflection element 92 is mounted to be pivotably movable about a further axis of rotation 120 parallel to the axis of rotation 118 and can be moved about the axis of rotation 120 in the direction of the further double-headed arrow 119.

In the first switching state shown in FIG. 8A, the beam splitter element 94 is pivoted into the stereoscopic partial observation beam path 24. The deflection element 92 is here arranged outside the stereoscopic partial observation beam path 24. The light from the first stereoscopic partial observation beam path 24 is split here by way of the beam splitter element 94 among the first beam path 80 and the second beam path 82 at the split ratio V=75%/25%.

In the second switching state shown in FIG. 8B, the deflection element 92 is pivoted into the stereoscopic partial observation beam path 24. The light is here deflected in its entirety from the first stereoscopic partial observation beam path 24 into the second beam path 82 by way of the deflection element 92.

In the third switching state shown in FIG. 8C, both the beam splitter element 94 and the deflection element 92 are located outside the stereoscopic partial observation beam path 24. In other words, the beam path switching device 72 here releases the stereoscopic partial observation beam path 24.

Figure 9A:
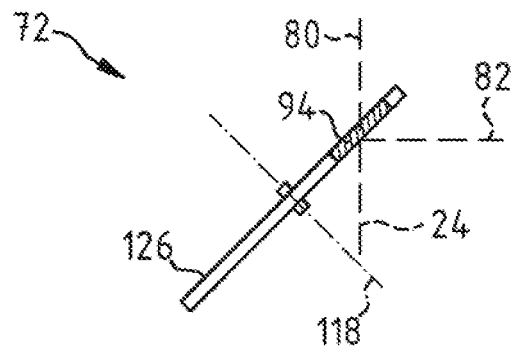
FIG. 9A and FIG. 9B show different views of a further beam path switching device for use in the surgical microscope.
Figure 9B:
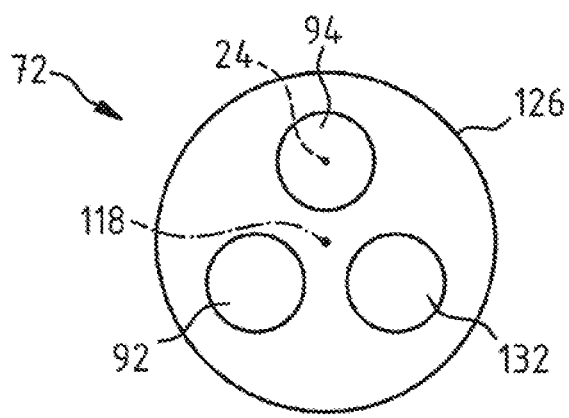

FIG. 9A and FIG. 9B show a further beam path switching device 72 in different views that is suitable for use in the surgical microscope 10. The beam path switching device 72 has a carrier apparatus 126 that is rotatable about an axis of rotation 118 of the type of a stop wheel having a beam splitter element 94 in the form of a splitter plate secured therein and a deflection element 92 in the form of a mirror secured therein. Additionally, a clear passage-opening 132 for light is located in the carrier apparatus 126.

FIG. 9A shows the beam path switching device 72 with a first stereoscopic partial observation beam path 24 and also with the first beam path 80 and the further beam path 82 in section in a setting in which the beam splitter element 94 is arranged in the stereoscopic partial observation beam path 24. FIG. 9B is a plan view of the carrier apparatus 126 of the further beam path switching device 72.

Figure 10:
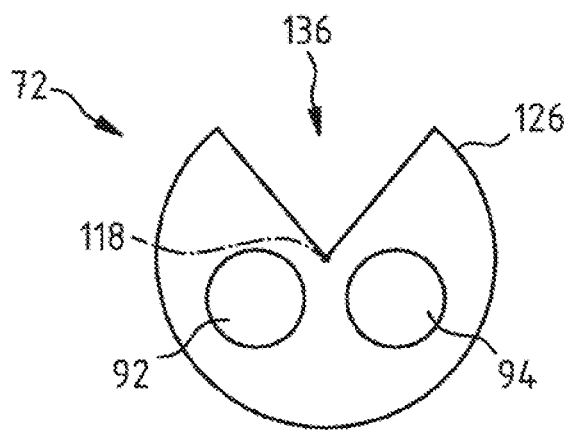
FIG. 10 shows a further beam path switching device for use in the surgical microscope.

FIG. 10 shows a further beam path switching device 72 for use in the surgical microscope 10 having a construction that corresponds to the beam path switching device 72 from FIG. 9A and FIG. 9B. Functionally identical assemblies of the beam path switching device 72 are designated with the same reference signs in FIG. 10 and in FIG. 9A and FIG. 9B. Unlike the beam path switching device 72 from FIG. 9A and FIG. 9B, the beam path switching device 72 has in the carrier apparatus 126 a cutout 136 in the form of a circular sector for releasing the stereoscopic partial observation beam path 24.

It should be noted that the beam path switching device 76 in the surgical microscope 10 described with reference to FIG. 1 to FIG. 4 can also have a construction that corresponds to the construction of the previously described beam path switching device 72.

It should in particular be noted that the previously described switching devices 72, 76 can in principle be configured such that it is possible therewith to switch two stereoscopic partial observation beam paths at the same time for stereoscopically observing the object region 12 by way of an adjustable deflection element 92 and an adjustable beam splitter element being able to be arranged on account of their geometric extent in the manner of a large optical unit through which a first and a second stereoscopic partial observation beam path extend simultaneously in a first and second stereoscopic partial observation beam path in each case for simultaneously switching the first and second stereoscopic partial observation beam path.

Figure 11A:
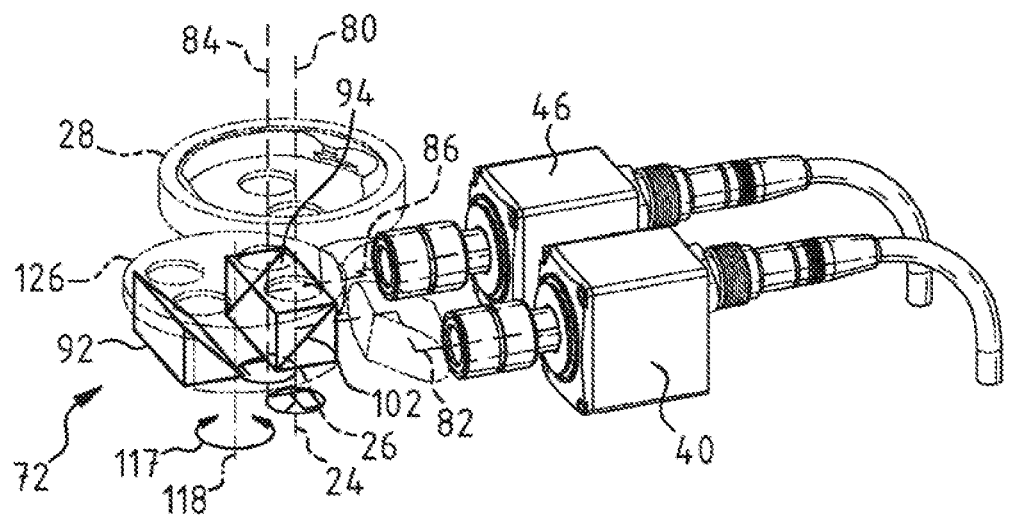
FIG. 11A and FIG. 11B show a further beam path switching device for use in a surgical microscope for stereoscopically visualizing an object region, with which two different switching states are settable.
Figure 11B:
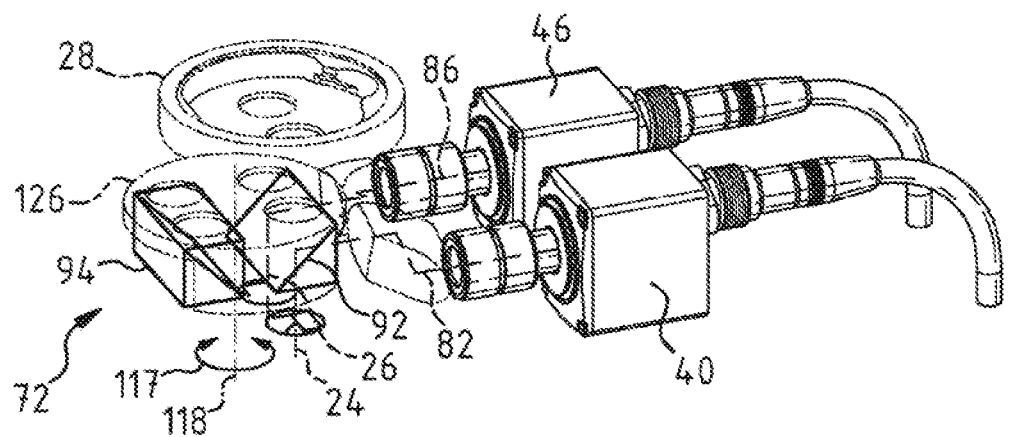

FIG. 11A and FIG. 11B show a further beam path switching device 72 in different switching states that is suitable for use in a surgical microscope that corresponds to the previously described surgical microscope 10. The beam path switching device 72 has a carrier apparatus 126 that is rotatable about an axis of rotation 118, parallel to the optical axis of the stereoscopic partial observation beam paths 24, 26, in accordance with the double-headed arrow 117, having a deflection element 92 in the form of a deflection prism and a beam splitter element 94 in the form of a splitter prism.

In the first switching state of the beam path switching device 72, shown in FIG. 11A, the beam splitter element 94 is arranged in the first stereoscopic partial observation beam path 24 and the second stereoscopic partial observation beam path 26. The light that is guided from the stereoscopic partial observation beam paths 24 and 26 to the beam splitter element 94 is then split by way of the splitter layer 102 in the beam splitter element 94 among the first beam path 80 and the second beam path 82, and among the further first beam path 84 and the further second beam path 86, respectively.

In the second switching state of the beam path switching device 72, shown in FIG. 11B, the deflection element 92 is arranged in the first stereoscopic partial observation beam path 24 and the second stereoscopic partial observation beam path 26, and the beam splitter element 94 is arranged outside the two stereoscopic partial observation beam paths 24 and 26. Here, the beam path switching device 72 steers the light from the first stereoscopic partial observation beam path 24 and the second stereoscopic partial observation beam path 26 into the second beam path 82 or the further second beam path 86 by way of the deflection element 92. However, it should be noted that the beam path switching device described with reference to FIG. 11A and FIG. 11B can not completely release the stereoscopic partial observation beam paths.

Figure 12A:
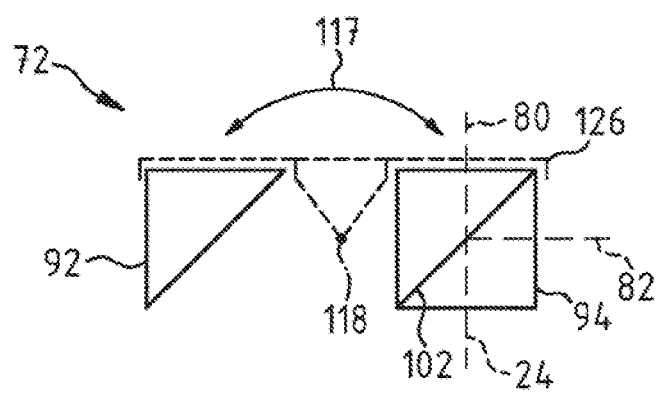
FIG. 12A and FIG. 12B show a further beam path switching device for use in a surgical microscope for stereoscopically visualizing an object region, with which two different switching states are settable.
Figure 12B:
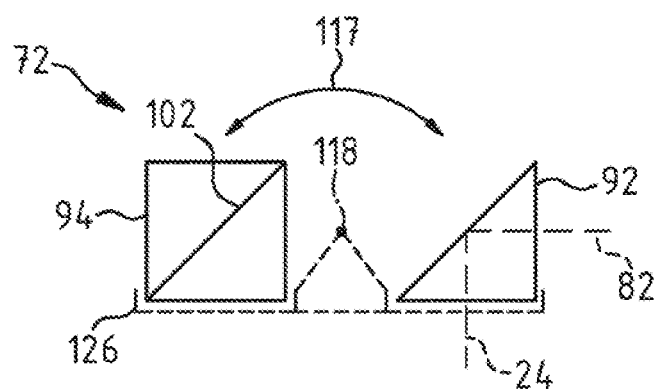

FIG. 12A and FIG. 12B show a further beam path switching device 72 in different switching states that is suitable for use in the surgical microscope 10. The beam path switching device 72 has a carrier apparatus 126 that is rotatable about an axis of rotation 118, perpendicular to the optical axis of the stereoscopic partial observation beam path 24, in accordance with the double-headed arrow 117, having a deflection element 92 in the form of a deflection prism and having a beam splitter element 94 in the form of a splitter cube.

In the first switching state of the beam path switching device 72 shown in FIG. 12A, the beam splitter element 94 is arranged in the stereoscopic partial observation beam path 24. The light that is guided from the stereoscopic partial observation beam path 24 to the beam splitter element 94 is then split by way of the splitter layer 102 in the beam splitter element 94 among the first beam path 80 and the second beam path 82.

In the second switching state of the beam path switching device 72 shown in FIG. 12B, the carrier apparatus 126 with the beam splitter element 94 that is held thereon and the deflection element 92 that is held thereon is rotated about the axis of rotation 118 through the angle of rotation $\alpha=180°$ with respect to the first switching state. In the second switching state of the beam path switching device 72, the deflection element 92 is arranged in the stereoscopic partial observation beam path 24 and the beam splitter element 94 is arranged outside the stereoscopic partial observation beam path 24. The beam path switching device 72 here steers the light from the first stereoscopic partial observation beam path 24 into the second beam path 82 by way of the deflection element 92.

It should be noted that the beam path switching device 76 in the surgical microscope 10 described with reference to FIG. 1 to FIG. 4 can have a construction that corresponds to the construction of the previously described beam path switching device 72.

It should also be noted that the previously described switching devices 72, 76 can in principle be configured such that it is possible therewith to switch two stereoscopic partial observation beam paths 24, 26 at the same time for stereoscopically observing the object region 12 by way of an adjustable deflection element 92 and an adjustable beam splitter element being able to be arranged on account of their geometric extent in the manner of a large optical unit through which a first and a second stereoscopic partial observation beam path 24, 26 extend simultaneously in a first and second stereoscopic partial observation beam path in each case for simultaneously switching the first and second stereoscopic partial observation beam path 24, 26. However, it should be noted that the beam path switching devices described with reference to FIG. 12A and FIG. 12B can again not completely release the stereoscopic partial observation beam paths 24, 26.

Moreover, it should be noted that the previously described switching devices 72, 76 can be configured such that via a rotational movement of the carrier apparatus 126 about the axis of rotation 118 through an angle of rotation $\alpha$ that differs from 180° can be transferred from the first switching state in which the beam splitter element 94 is arranged in the stereoscopic partial observation beam path 24 or the stereoscopic partial observation beam path 26 into the second switching state in which the deflection element 92 is located in the stereoscopic partial observation beam path 24 or the stereoscopic partial observation beam path 26.

FIG. 12C and FIG. 12D show a further beam switching device 72 having a carrier apparatus 126 that can be transferred by a rotational movement about the axis of rotation 118 through the angle of rotation $\alpha=90°$ from the first switching state in which the beam splitter element 94 is arranged in the stereoscopic partial observation beam path 24 into the second switching state in which the deflection element 92 is located in the stereoscopic partial observation beam path 24.

Figure 13A:
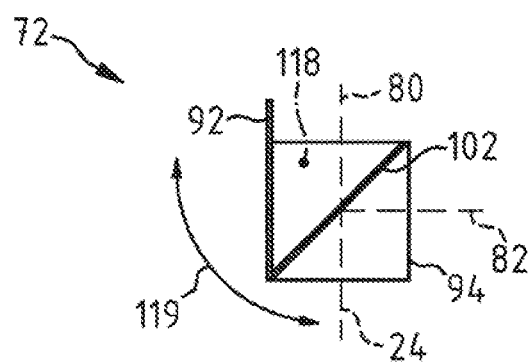
FIG. 13A and FIG. 13B show a further beam path switching device for use in a surgical microscope for stereoscopically visualizing an object region, with which two different switching states are settable.
Figure 13B:
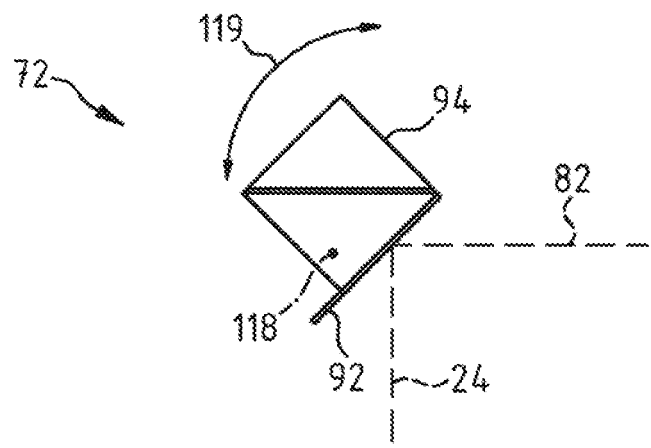

FIG. 13A and FIG. 13B show a further beam path switching device 72' in different switching states that is suitable for use in a surgical microscope that corresponds to the surgical microscope 10. The beam path switching device 72' has a carrier apparatus, which is rotatable about an axis of rotation 118, located in a plane perpendicular to the optical axis of the stereoscopic partial observation beam path 24, corresponding to the double-headed arrow 119, and has a beam splitter element 94 in the form of a splitter cube and a deflection element 92 in the form of a plane mirror formed on a face of the splitter cube.

In the first switching state of the beam path switching device 72 shown in FIG. 13A, the beam splitter element 94 is arranged in the stereoscopic partial observation beam path 24. The light that is guided from the stereoscopic partial observation beam path 24 to the beam splitter element 94 is then split by way of the splitter layer 102 in the beam splitter element 94 among the first beam path 80 and the second beam path 82.

In the second switching state of the beam path switching device 72 shown in FIG. 13B, the deflection element 92 deflects the light from the first stereoscopic partial observation beam path 24 into the first beam path 80.

It should be noted that the beam path switching device 76 in the surgical microscope 10 described with reference to FIG. 1 to FIG. 4 can also in principle have a construction that corresponds to the construction of the previously described beam path switching device 72. However, it should be noted that the beam path switching device described with reference to FIG. 13A and FIG. 13A can again not completely release the stereoscopic partial observation beam paths 24, 26.

It should furthermore be noted that the previously described switching devices 72, 76 can in principle also be configured for simultaneously switching the two stereoscopic partial observation beam paths 24, 26 for stereoscopically observing the object region 12, for example by way of an adjustable deflection element 92 and an adjustable beam splitter element being arrangeable on account of their geometric extent in the manner of a large optical unit through which a first and a second stereoscopic partial observation beam path 24, 26 extend simultaneously in a first and second stereoscopic partial observation beam path in each case for simultaneously switching the first and second stereoscopic partial observation beam path 24, 26.

FIG. 14A and FIG. 14B show a further beam path switching device 72 in different switching states that is suitable for use in a surgical microscope that corresponds to the previously described surgical microscope 10. The beam path switching device 72 has a deflection element 92 in the form of a deflection prism and a splitter prism in the form of the beam splitter element 94 and also a light trap 100. The deflection element 92 and the beam splitter element 94 are arranged on a common carrier apparatus 126 that is displaceable such that it moves linearly in the direction of the double-headed arrow 96.

In the first switching state of the beam path switching device 72 shown in FIG. 14A, the beam splitter element 94 is arranged in the manner of a large optical unit through which two stereoscopic partial observation beam paths extend at the same time in the first stereoscopic partial observation beam path 24 and in the second stereoscopic partial observation beam path 26. The light that is guided from the stereoscopic partial observation beam paths 24 and 26 to the beam splitter element 94 is split here at a splitter layer 102 in the beam splitter element 94 among the first beam path 80 and the second beam path 82, and among the further first beam path 84 and the further second beam path 86, respectively.

In the second switching state of the beam path switching device 72, shown in FIG. 14B, the deflection element 92 is arranged in the stereoscopic partial observation beam path 24 and the stereoscopic partial observation beam path 26. In this switching state, the beam splitter element 94 is located outside the stereoscopic partial observation beam path 24 and the stereoscopic partial observation beam path 26. In the switching state shown in FIG. 14B, the beam path switching device 72 steers the light from the stereoscopic partial observation beam path 24, 26 through the beam splitter element 94 by way of the deflection element 92. The light from the stereoscopic partial observation beam paths 24, 26 is split at the splitter layer 102 in the beam splitter element 94 among the beam paths 82, 86, 104 and 104'. The beam paths 104, 104' here extend to the light trap 100 that receives the light from the beam paths, with the result that no stray light that disturbs the observation image and no reflection that disturbs the observation image is produced in the surgical microscope 10.

Figure 14C:
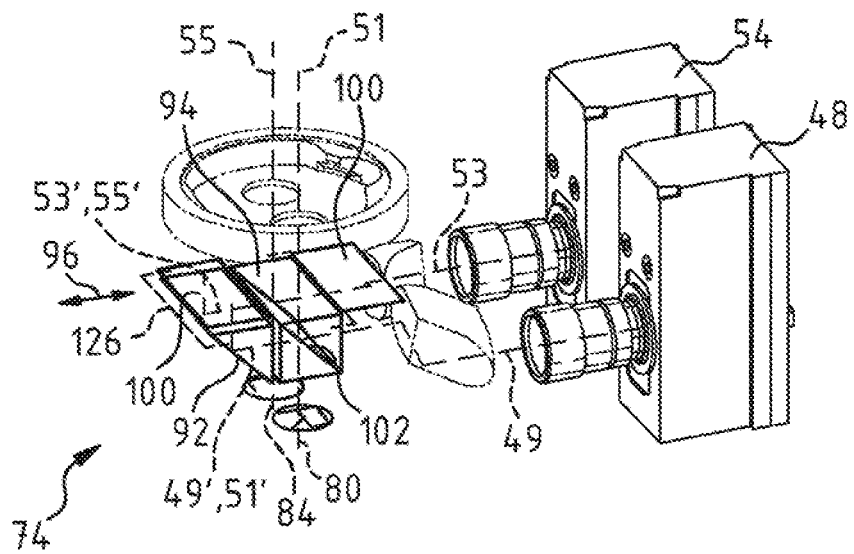
Figure 14D:
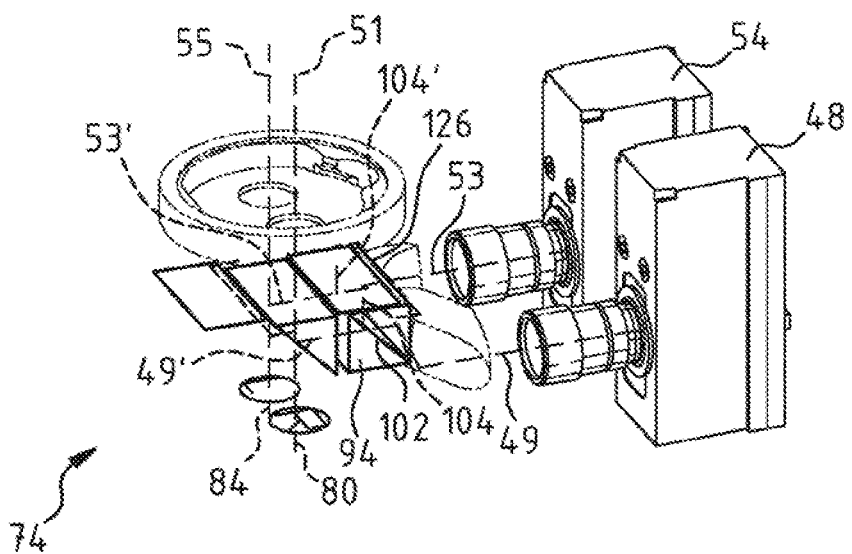

FIG. 14C and FIG. 14D show a further beam path switching device 74 in different switching states that is suitable for use in a surgical microscope that corresponds to the previously described surgical microscope 10. The beam path switching device 74 likewise has a deflection element 92 in the form of a deflection prism and a splitter prism in the form of the beam splitter element 94 and also two light traps 100. The deflection element 92 and the beam splitter element 94 are arranged here, too, on a common carrier apparatus 126 that is displaceable such that it moves linearly in the direction of the double-headed arrow 96.

In the first switching state of the beam path switching device 74, shown in FIG. 14C, the beam splitter element 94 is arranged in the first beam path 80 and the second beam path 82. The light that is guided from the beam paths 80 and 82 to the beam splitter element 94 is split here at a splitter layer 102 in the beam splitter element 94 among the first beam path 51 to the first eyepiece 32 and a further beam path 51' and among the beam path 55 to the further eyepiece 34 and a further beam path 55'. The light that is guided from the display beam paths 49, 53 to the beam splitter element 94 is split here at a splitter layer 102 in the beam splitter element 94 among the first beam path 51 to the first eyepiece 32 and a further beam path 49' and among the further first beam path 55 to the second eyepiece 34 and a further beam path 53'.

The beam splitter element 94 thus superposes the first display beam path 49 and the second display beam path 53 on the first beam path 80 and the further first beam path 84. The beam paths 51', 55' reflected at the splitter layer 102 in the beam splitter element 94 from the beam paths 80, 84 and the beam paths 49' and 53' transmitted at the splitter layer 102 in the beam splitter element 94 from the display beam paths 49, 53 are guided by way of the deflection element 92 to the light trap 100. In this way, the light that is guided in the beam path 51', 55' and 49', 53' produces no stray light in the surgical microscope that disturbs the observation image and no reflection that disturbs the observation image.

In the second switching state shown in FIG. 14D, the beam path switching device 74 steers the light by way of the deflection element 92 from the display beam paths 49 and 53, which extend through the beam splitter element 94, into the beam path 51 to the first eyepiece 32 and the beam path 55 to the second eyepiece 34. The light from the display beam paths 49, 53 is split at the splitter layer 102 in the beam splitter element 94 among the beam path 49', 53' to the deflection element, and a further beam path 104 and 104'. The further beam path 104, 104' is guided into the further light trap 100, which receives the light from the beam path 104, 104'. In this way, the light that is guided in the further beam path 104, 104' produces no stray light in the surgical microscope that disturbs the observation image and no reflection that disturbs the observation image.

FIG. 15A and FIG. 15B and FIG. 15C show a further beam path switching device 74 in different switching states for use in a surgical microscope that corresponds to the surgical microscope 10. This beam path switching device 74 likewise has a deflection element 92 in the form of a deflection prism and contains a beam splitter element 94 in the form of a splitter cube. The deflection element 92 and the beam splitter element 94 are arranged on a carrier element 98 that is displaceable in the surgical microscope 10 in the direction of the double-headed arrow 96 preferably perpendicularly to the first beam path 80. For setting the different switching states of the beam path switching device 74, the carrier element 98 with the deflection element 92 arranged thereon and the beam splitter element 94 is displaced in the direction of the double-headed arrow 96. The beam path switching device 74 has a first and a second light trap 100 that are arranged in a locationally fixed manner in the surgical microscope 10.

In the first switching state of the beam path switching device 74 shown in FIG. 15A, the light is guided from the first display beam path 49 through the beam splitter element 94. This light is split at the splitter layer 102 among a beam path 51 to the first eyepiece 32 and a further beam path 49' to the deflection element 92. The deflection element 92 steers the beam path 49' into the beam path 49" to the first light trap 100.

The light reflected at the splitter layer 102 of the beam splitter element 94 from the beam path 80 into the beam path 51' is likewise deflected by way of the deflection element 92 into beam path 51" to the first light trap 100, which receives the light. In this way, the light that is guided in the beam path 49', 49", 51', 51" produces no stray light in the surgical microscope 10 that disturbs the observation image and no reflection that disturbs the observation image.

By contrast, the beam path switching device 74 in the second switching state, shown in FIG. 15B, steers the light from the first display beam path 49, which extends through the beam splitter element 92, into the beam path 51 to the first eyepiece 32 by way of the deflection element 92. The light from the display beam path 49 is split at the splitter layer 102 in the beam splitter element 94 among the beam path 49' to the deflection element, and a further beam path 104. The further beam path 104 is guided into the second light trap 100, which receives the light from the beam path 104. In this way, the light that is guided in the further beam path 104 produces no stray light in the surgical microscope 10 that disturbs the observation image and no reflection that disturbs the observation image.

In the third switching state shown in FIG. 15C, the beam path switching device 74 releases the beam path 80 in the surgical microscope 10. In this switching state, the beam path 80 is transferred into the beam path 51 to the first eyepiece 32.

In order to prevent the production of disturbing stray light in a surgical microscope, it may make sense in this switching state of the beam path switching device 74 that no image signals are then provided by way of display devices 48, 54.

Figure 16A:
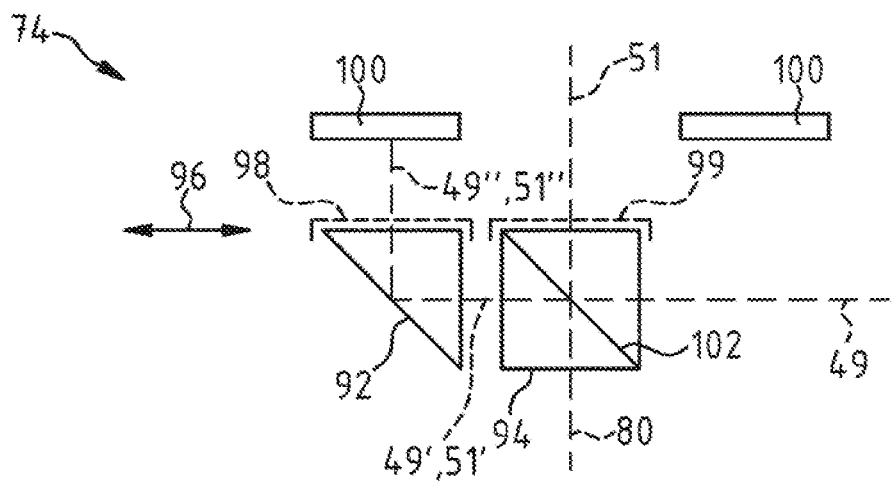
FIG. 16A and FIG. 16B and FIG. 16C show a further beam path switching device in different switching states for use in a surgical microscope for stereoscopically visualizing an object region.
Figure 16B:
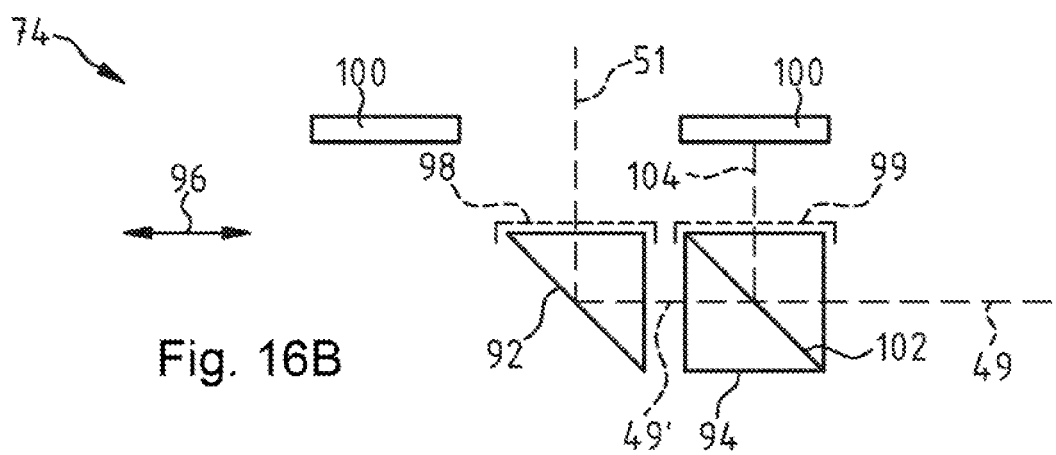
Figure 16C:
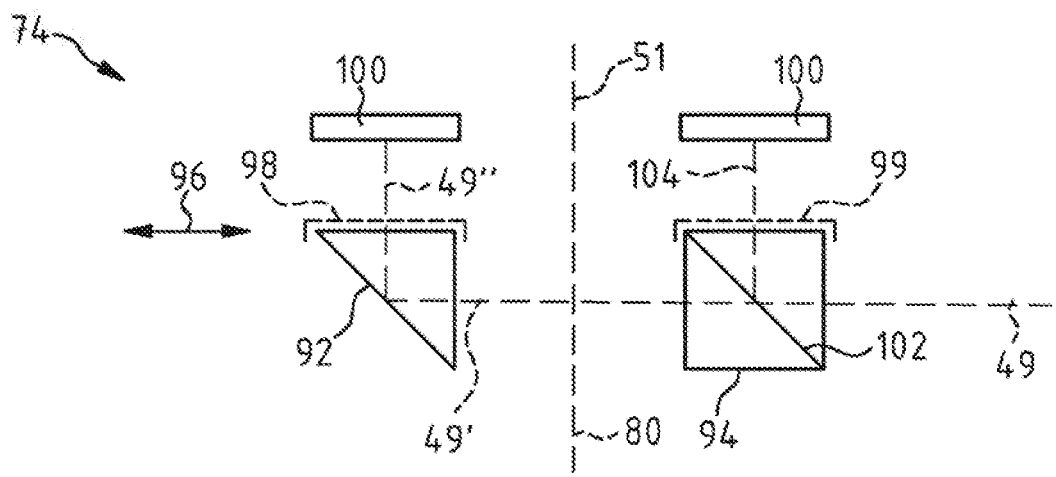

FIG. 16A and FIG. 16B and FIG. 16C show a further beam path switching device 74 in different switching states that is suitable for use in a surgical microscope that corresponds to the previously described surgical microscope 10 for switching the first beam path 80. The beam path switching device 74 also contains a deflection element 92 in the form of a deflection prism and has a beam splitter element 94, in the form of a splitter cube, with a splitter layer 102. The deflection element 92 and the beam splitter element 94 are likewise held here on carrier elements 98, 99 that are arranged in a surgical microscope 10 so as to be displaceable relative to one another and relative to the first beam path 80 in the direction of the double-headed arrow 96 perpendicularly to the first beam path 80. A first and a second light trap 100 that are arranged in a locationally fixed manner with respect to the first beam path 80 in the surgical microscope 10 are also present in the beam path switching device 74.

For setting the different switching states of the beam path switching device 74, the deflection element 92 that is secured on the carrier element 98 and the beam splitter element 94 that is secured on the carrier element 99 are each displaced in the direction of the double-headed arrow 96 with respect to the first beam path 80.

In the first switching state shown in FIG. 16A, the light in the beam path switching device 74 is guided from the display beam path 49 into the beam splitter element 94. The light from the display beam path 49 is split at the splitter layer 102 in the beam splitter element 94 into a beam path 51 to the eyepiece 32 and into a beam path 49' to the deflection element 92. The latter steers the light in the beam path 49" into the light trap 100.

The light reflected at the splitter layer 102 of the beam splitter element 94 from the beam path 80 into the beam path 51' is likewise deflected here by way of the deflection element 92 into beam path 51" to the light trap 100, which receives the light. In this way, the light that is guided in the beam path 49', 49", 51', 51" produces no stray light in the surgical microscope 10 that disturbs the observation image and no reflection that disturbs the observation image.

By contrast, the beam path switching device 74 in the second switching state, shown in FIG. 16B, is used to steer the light from the display beam path 49, which extends through the beam splitter element 94, from the beam path 49' into the beam path 51 to the eyepiece 32 by way of the deflection element 92.

In the beam splitter element 94, the light from the display beam path 49 is split into the beam path 49' and the beam path 104. The further beam path 104 is then guided into the second light trap 100, which receives the light from the beam path 104. In this way, the light that is guided in the further beam path 104 produces no stray light in the surgical microscope 10 that disturbs the observation image and no reflection that disturbs the observation image.

In the switching state shown in FIG. 16C, the beam path switching device 74 releases the beam path 80. In this switching state, the beam path 80 is transferred into the beam path 51 to the first eyepiece 32. In order to prevent the production of disturbing stray light in a surgical microscope 10, it may make sense in this switching state of the beam path switching device 74 that no image signals are then provided by way of display devices 48, 54.

Figure 17A:
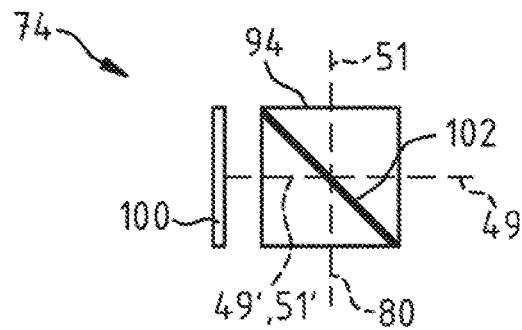
FIG. 17A and FIG. 17B and FIG. 17C show a further beam path switching device in different switching states for use in a surgical microscope for stereoscopically visualizing an object region.
Figure 17B:
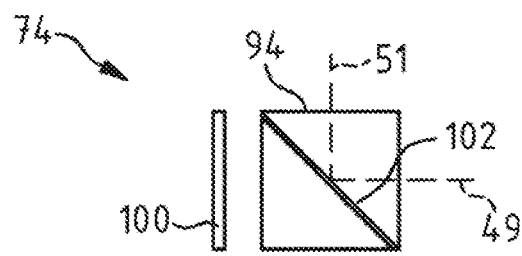
Figure 17C:
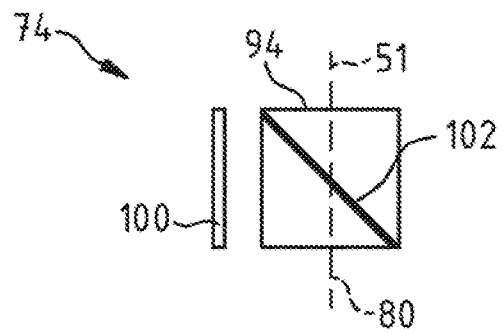

FIG. 17A and FIG. 17B and FIG. 17C show a further beam path switching device 74 in different switching states that is suitable for use in a surgical microscope that corresponds to the previously described surgical microscope 10.

The beam path switching device 74 contains a beam splitter element, in the form of a splitter cube, with an electrically controllable splitter layer 102 and a light trap 100. The splitter layer 102 can again, for example, have a construction as described in U.S. Pat. No. 6,999,649 B, to which reference is made herewith in the entirety thereof and the disclosure of which is incorporated into the description of this invention. In that case, the splitter layer 102 is embodied in the form of a layer having liquid crystals extending in a longitudinal direction, the orientation of which can be varied by setting a voltage and that reflect the light that is incident on the splitter layer 102 in dependence on the orientation of the liquid crystals.

In the first switching state shown in FIG. 17A, the beam path switching device 74 superposes onto the light in the beam path 80, which passes through the splitter layer 102, that portion of the light from the display beam path 49 which the splitter layer 102 in the beam splitter element 94 reflects into the beam path 51 to the first eyepiece 32. The splitter layer 102 in the beam splitter element 94 in this case has the effect that for example 90% of the light is transmitted from the beam path 80 into the beam path 51 and only 10% of the light is reflected into the beam path 51'. In this way, it is possible to ensure that an image quality and image brightness for observing the object region 12 in a surgical microscope 10 with a purely optical observation beam path is not significantly impaired by the beam splitter element 94. The light reflected at the splitter layer 102 of the beam splitter element 94 from the beam path 80 into the beam path 51' and transmitted thereby from the beam path 49 into the beam path 49' is guided here to the light trap 100, which receives the light. In this way, the light that is guided in the beam path 49', 51' produces no stray light in the surgical microscope 10 that disturbs the observation image and no reflection that disturbs the observation image.

By contrast, the beam path switching device 74 in the second switching state, shown in FIG. 17B, is used to reflect the light from the display beam path 49 into the beam path 51 to the first eyepiece 32. The splitter layer 102 in the beam splitter element 94 preferably reflects in this case all light from the display beam path 49 into the beam path 51.

In the third switching state shown in FIG. 17C, the light is split in the beam splitter element 94 from the beam path 80 among the beam path 51 and the beam path to the light trap, for example, with the split ratio Q=100%/0%. In this switching state, no light is thus guided from the display beam path 49 to the beam path 51.

Figure 18A:
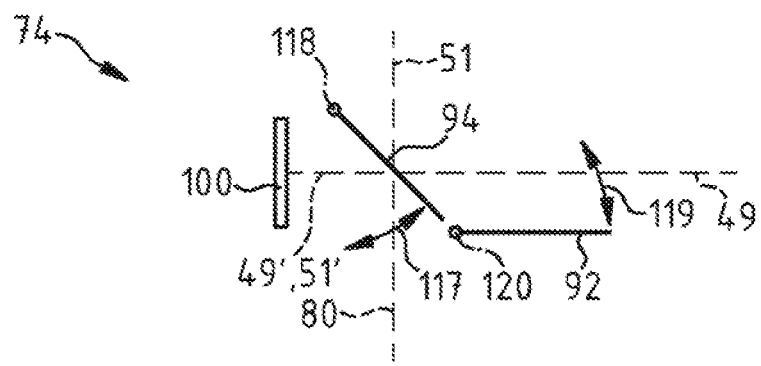
FIG. 18A and FIG. 18B and FIG. 18C show a further beam path switching device in different switching states for use in a surgical microscope for stereoscopically visualizing an object region.
Figure 18B:
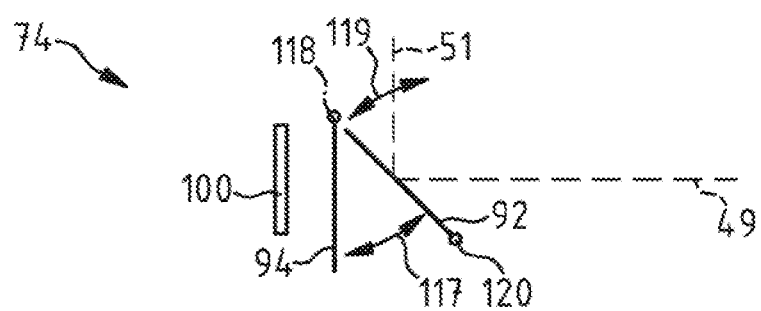
Figure 18C:
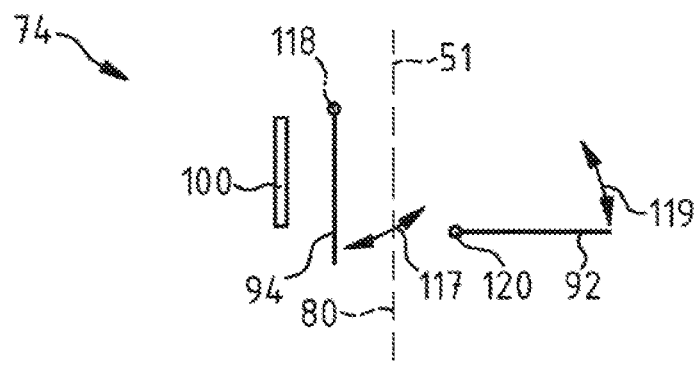

FIG. 18A and FIG. 18B and FIG. 18C show a further beam path switching device 74 in different switching states that is suitable for use in a surgical microscope that corresponds to the previously described surgical microscope 10. The beam path switching device 74 contains a beam splitter element 94, in the form of a splitter plate, and a deflection element 92 in the form of a folding mirror. The beam splitter element 94 in the beam path switching device 74 can be pivoted about an axis of rotation 118 in accordance with the double-headed arrow 117. The deflection element 92, in the form of a folding mirror, is mounted to be pivotably movable about a further axis of rotation 120 parallel to the axis of rotation 118 and can be moved about the axis of rotation 120 in the direction of the further double-headed arrow 119.

In the first switching state shown in FIG. 18A, the beam splitter element 94 is pivoted into the first beam path 80. The deflection element 92 is here arranged outside the beam path 80 and 49. The light from the display beam path 49 is split here by way of the beam splitter element 94 among the first beam path 51 to the first eyepiece 32 and a further beam path 49'. The light from the beam path 80 is split at the splitter layer 102 in the beam splitter element 94 into the beam path 51 to the first eyepiece 32 and into the further beam path 51'. The light reflected at the splitter layer 102 of the beam splitter element 94 from the beam path 80 into the beam path 51' and transmitted thereby from the beam path 49 into the beam path 49' is guided here to the light trap 100, which receives the light. In this way, the light that is guided in the beam path 49', 51' produces no stray light in the surgical microscope 10 that disturbs the observation image and no reflection that disturbs the observation image.

In the second switching state shown in FIG. 18B, the deflection element 92 is pivoted into the display beam path 49. The light from the display beam path 49 is steered here by way of the deflection element 92 in its entirety into the beam path 51 to the first eyepiece 32.

In the third switching state shown in FIG. 18C, both the beam splitter element 94 and the deflection element 92 are located outside the beam path 80. In this case, the beam path switching device 74 thus releases the beam path 80 in the surgical microscope 10, with the result that the beam path 80 is transferred into the beam path 51 to the first eyepiece 32. In order to prevent the production of disturbing stray light in a surgical microscope 10, it may make sense in this switching state of the beam path switching device 74 that no image signals are then provided by way of display devices 48, 54.

FIG. 19A and FIG. 19B show a further beam path switching device 74 in different views that is suitable for use in a surgical microscope that corresponds to the previously described surgical microscope 10. The beam path switching device 74 has a carrier apparatus 126 that is rotatable about an axis of rotation 118 of the type of a stop wheel having a splitter plate in the form of a beam splitter element 94 secured therein and a deflection element 92 in the form of a mirror secured therein. Additionally, a clear passage-opening 132 for light and a light trap 100 are located in the carrier apparatus 126.

FIG. 19A shows the beam path switching device 74 with the beam path 80 and the display beam path 49 and also with the beam path 51 to the first eyepiece 32 in section in a setting in which the beam splitter element 94 is arranged in the beam path 80 and the display beam path 49. FIG. 19B is a plan view of the carrier apparatus 126 of the further beam path switching device 74.

FIG. 20 shows a further beam path switching device 74 for use in the surgical microscope 10 having a construction that corresponds to the previously described beam path switching device. Assemblies of the beam path switching device 74 that are functionally identical to the assemblies of the beam path switching device 74 of FIG. 19A and FIG. 19B are designated with the same reference signs in FIG. 20 and in FIG. 19A and FIG. 19B. Unlike the beam path switching device from FIG. 19A and FIG. 19B, the beam path switching device 74 has in the carrier apparatus 126 a cutout 136 in the form of a circular sector as a free passage-opening for light for releasing the stereoscopic partial observation beam path 24.

It should be noted that the beam path switching device 78 in the surgical microscope 10 described with reference to FIG. 1 to FIG. 4 can have a construction that corresponds to the construction of the previously described beam path switching devices 74.

It should in particular be noted that the previously described switching devices 74, 78 can in principle be configured such that it is possible therewith to switch two stereoscopic partial observation beam paths at the same time for stereoscopically observing the object region 12 by way of an adjustable deflection element 92 and an adjustable beam splitter element being able to be arranged on account of their geometric extent in the manner of a large optical unit through which a first and a second stereoscopic partial observation beam path simultaneously extend in a first and second stereoscopic partial observation beam path in each case for simultaneously switching the first and second stereoscopic partial observation beam path.

Figure 21A:
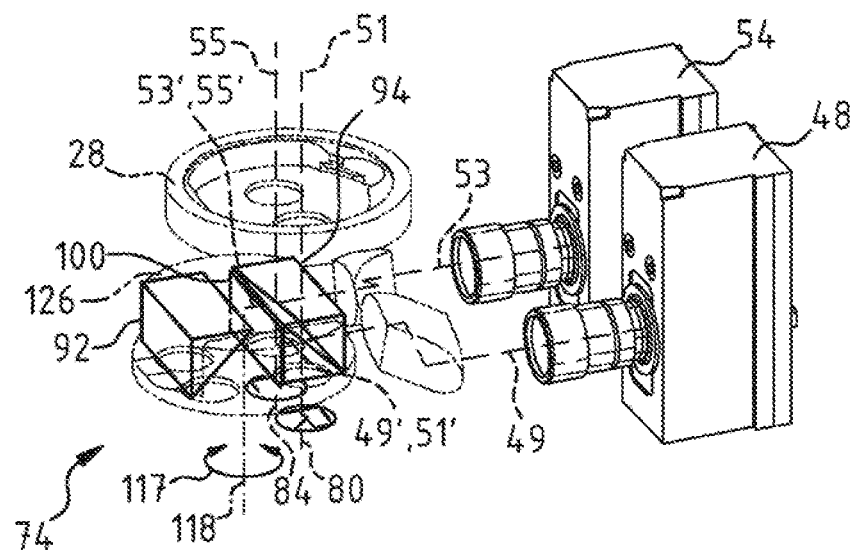
FIG. 21A and FIG. 21B show a further beam path switching device for use in a surgical microscope for stereoscopically visualizing an object region, with which two different switching states are settable.
Figure 21B:
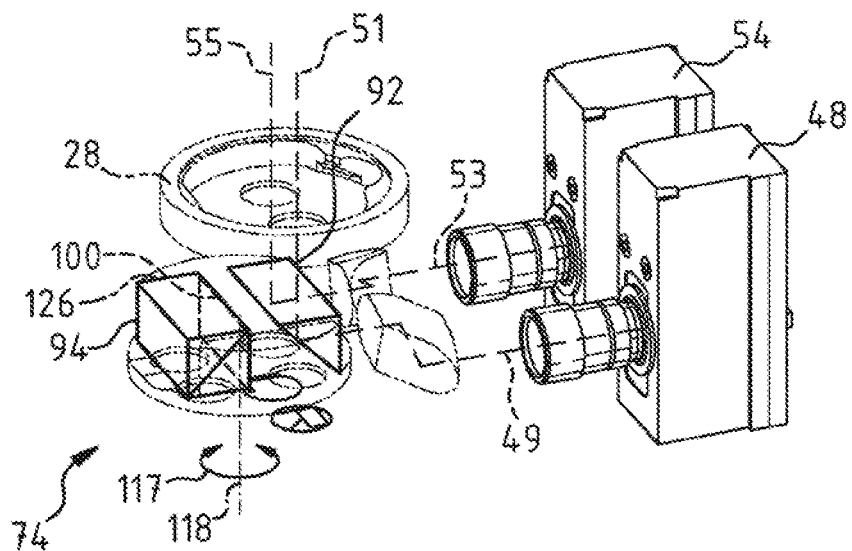

FIG. 21A and FIG. 21B show a further beam path switching device 74 in different switching states that is suitable for use in the surgical microscope 10. The beam path switching device 74 has a carrier apparatus 126 that is rotatable about an axis of rotation 118, parallel to the optical axis of the beam path 80, in accordance with the double-headed arrow 117, having a deflection element 92 in the form of a deflection prism and a beam splitter element 94 in the form of a splitter prism.

In the first switching state of the beam path switching device 74, shown in FIG. 21A, the beam splitter element 94 is arranged in the first beam path 80 and the further first beam path 84. The light that is guided from these beam paths to the beam splitter element 94 is then split by way of the splitter layer 102 in the beam splitter element 94 among the beam path 51 to the first eyepiece 32 and a further beam path 51' and among the beam path 55 to the further eyepiece 34 and a further beam path 55'. Accordingly, the light from the display beam path 49 provided by the first display device 48 and the light from the display beam path 53 provided by the second display device 54 is split in the beam splitter element 94 at the splitter layer 102 into the beam paths 51, 55 to the first and the second eyepiece 32, 34 and beam paths 49', 53'. The light reflected at the splitter layer 102 of the beam splitter element 94 from the beam paths 80, 84 into the beam paths 51', 55' and transmitted thereby from the beam paths 49, 53 into the beam paths 49', 53' is guided here to the light trap 100, which receives the light. In this way, the light that is guided in the beam path 49', 51', 53', 55' produces no stray light in the surgical microscope 10 that disturbs the observation image and no reflection that disturbs the observation image.

In the second switching state of the beam path switching device 74, shown in FIG. 21B, the deflection element 92 is arranged in the display beam path 49 and the display beam path 53, and the beam splitter element 94 is arranged outside the beam path 51 and the display beam path 53. Here, the beam path switching device 74 steers the light by way of the deflection element 92 from the display beam path 49 and the display beam path 53 into the beam path 51 to the first eyepiece 32 and the beam path 55 to the second eyepiece 34. However, it should be noted that the beam path switching device described with reference to FIG. 21A and FIG. 21B is not configured to facilitate the complete release of stereoscopic partial observation beam paths.

Figure 22A:
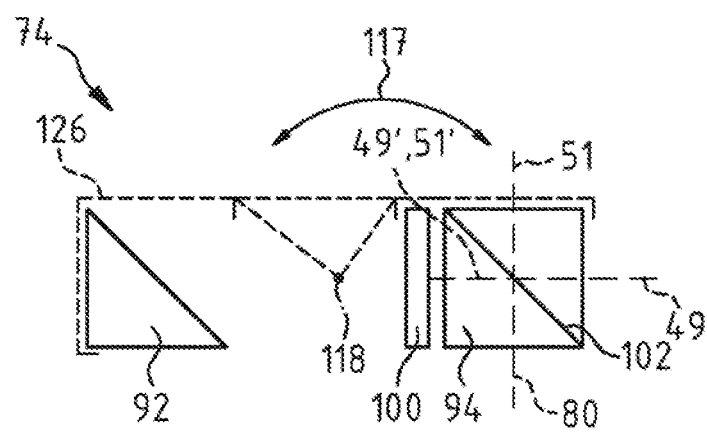
FIG. 22A and FIG. 22B show a further beam path switching device for use in a surgical microscope for stereoscopically visualizing an object region, with which two different switching states are settable.
Figure 22B:
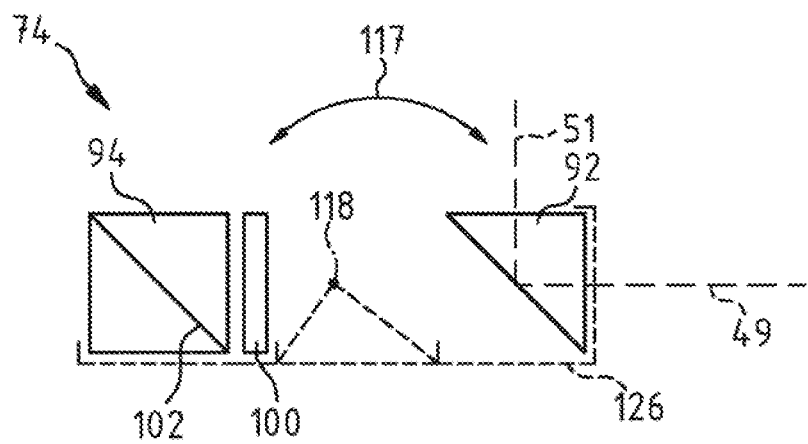

FIG. 22A and FIG. 22B show a further beam path switching device 74 in different switching states that is suitable for use in a surgical microscope that corresponds to the previously described surgical microscope 10. The beam path switching device 74 has a carrier apparatus 126 that is rotatable about an axis of rotation 118, perpendicular to the optical axis of the beam path 80, in accordance with the double-headed arrow 117, having a deflection element 92 in the form of a deflection prism, having a beam splitter element 94 in the form of a splitter cube and having a light trap 100.

In the first switching state of the beam path switching device 74 shown in FIG. 22A, the beam splitter element 94 is arranged in the beam path 80. The light that is guided from the beam path 80 to the beam splitter element 94 is then split at the splitter layer 102 in the beam splitter element 94 among the beam path 51 to the first eyepiece 32 and a further beam path 51' to the light trap 100. In addition, the light that is guided from the display beam path 49 to the beam splitter element 94 is then split at the splitter layer 102 in the beam splitter element 94 among the beam path 51 to the first eyepiece 32 and a further beam path 49' likewise to the light trap 100. In this way, the light that is guided in the beam path 49', 51' produces no stray light in the surgical microscope 10 that disturbs the observation image and no reflection that disturbs the observation image.

In the second switching state of the beam path switching device 74, shown in FIG. 22B, the deflection element 92 is arranged in the beam path 80, and the beam splitter element 94 is arranged outside the beam path 80. The beam path switching device 74 here steers the light from the display beam path 49 by way of the deflection element 92 into the beam path 51 to the first eyepiece 32.

It should be noted that the beam path switching device 78 in the surgical microscope 10 described with reference to FIG. 1 to FIG. 4 can have a construction that corresponds to the construction of the previously described beam path switching device 74. It should also be noted that the previously described switching devices 74, 78 can in principle be configured such that it is possible therewith to switch two stereoscopic partial observation beam paths at the same time for stereoscopically observing the object region 12 by way of an adjustable deflection element 92 and an adjustable beam splitter element being able to be arranged on account of their geometric extent in the manner of a large optical unit through which a first and a second stereoscopic partial observation beam path extend simultaneously in a first and second stereoscopic partial observation beam path in each case for simultaneously switching the first and second stereoscopic partial observation beam path. Such a beam path switching device, however, is not configured to facilitate the complete release of stereoscopic partial observation beam paths.

Figure 23A:
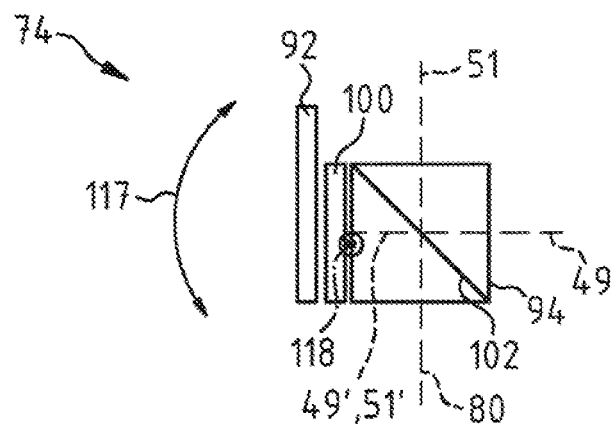
FIG. 23A and FIG. 23B show a further beam path switching device for use in a surgical microscope for stereoscopically visualizing an object region, with which two different switching states are settable.
Figure 23B:
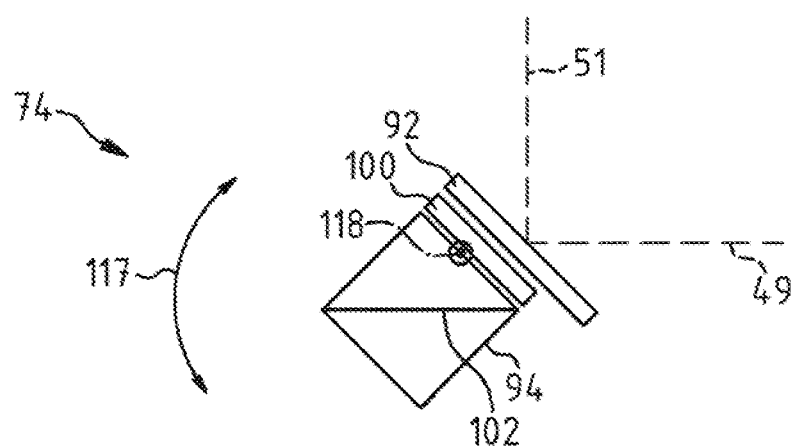

FIG. 23A and FIG. 23B show a further beam path switching device 74 in different switching states that is suitable for use in a surgical microscope that corresponds to the previously described surgical microscope 10. The beam path switching device 74 has a carrier apparatus, which is rotatable about an axis of rotation 118, located in a plane perpendicular to the optical axis of the beam path 80, corresponding to the double-headed arrow 117, and has a beam splitter element 94 in the form of a splitter cube, has a light trap 100, and has a deflection element 92 in the form of a plane mirror. By rotating the carrier apparatus about the axis of rotation 118, it is possible to selectively arrange the deflection element 92 or the beam splitter element 94 in the beam path 80.

In the first switching state of the beam path switching device 74, shown in FIG. 23A, the beam splitter element 94 is arranged such that the light from the display beam path 49 is superposed at the splitter layer 102 in the beam splitter element 94 on the light from the first beam path 80 and guided into the beam path 51 to the first eyepiece 32.

In the second switching state of the beam path switching device 74 shown in FIG. 23B, the deflection element 92 steers the light from the display beam path 49 into the beam path 51 to the first eyepiece 32.

It should be noted that the beam path switching device 78 in the surgical microscope 10 described with reference to FIG. 1 to FIG. 4 can have a construction that corresponds to the construction of the previously described beam path switching device 74. It should also be noted that the previously described switching devices 74, 78 can in principle be configured such that it is possible therewith to switch two stereoscopic partial observation beam paths at the same time for stereoscopically observing the object region 12 by way of an adjustable deflection element 92 and an adjustable beam splitter element being able to be arranged on account of their geometric extent in the manner of a large optical unit through which a first and a second stereoscopic partial observation beam path extend simultaneously in a first and second stereoscopic partial observation beam path in each case for simultaneously switching the first and second stereoscopic partial observation beam path. Such a beam path switching device, however, is not configured to facilitate the complete release of stereoscopic partial observation beam paths.

Figure 24:
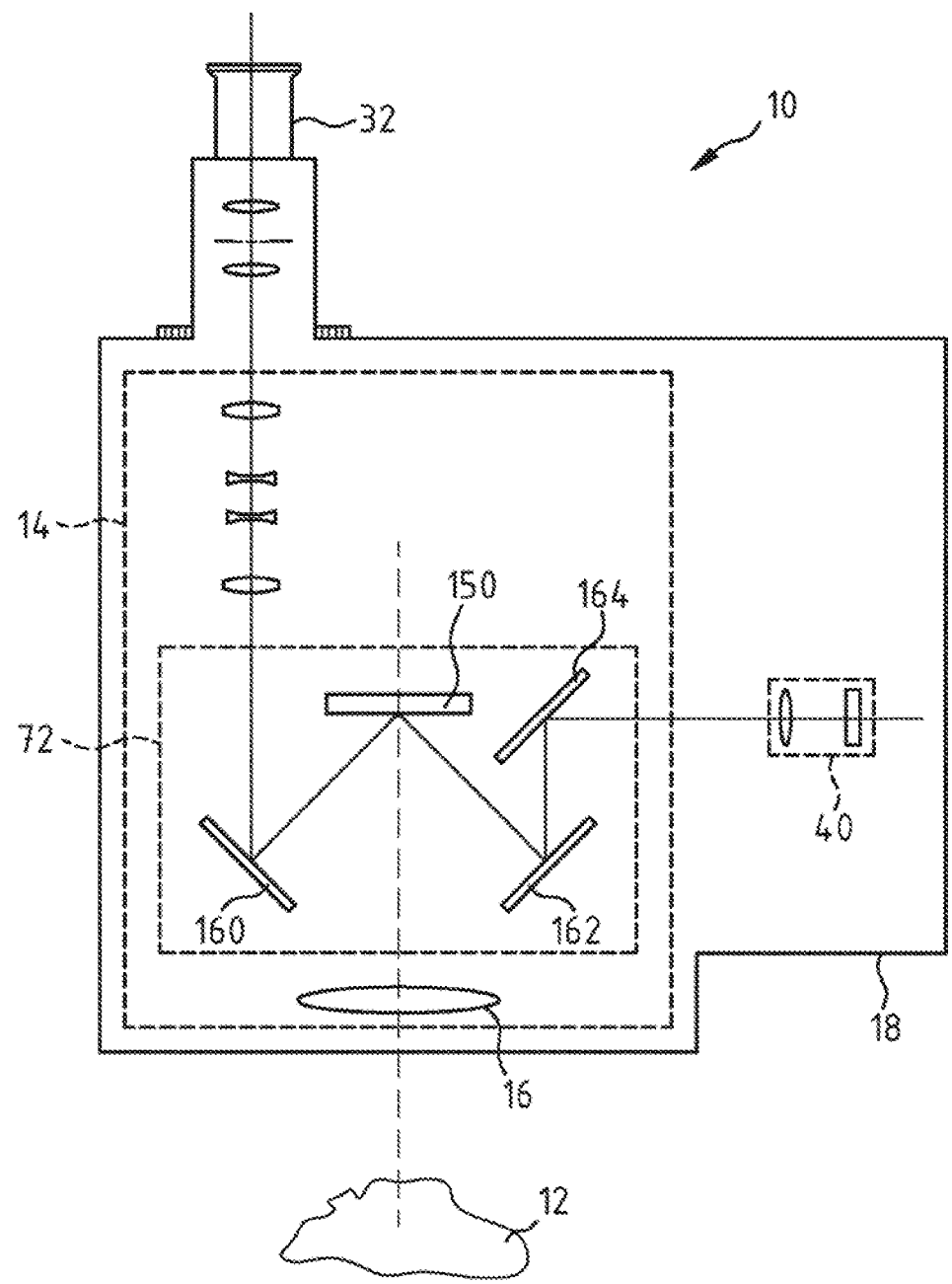
FIG. 24 shows a further surgical microscope for visualizing an object region.

The surgical microscope 10 shown in FIG. 24 serves for the magnified visualization of an object region 12. Where the assemblies of the surgical microscope 10 described above with reference to FIG. 1 to FIG. 4 functionally correspond to the assemblies of the surgical microscope 10 of FIG. 1, they are provided with the same numbers as reference signs.

The surgical microscope 10 has an imaging optical unit 14 with a microscope main objective system 16, the imaging optical unit being held in a main body 18. The imaging optical unit 14 of the surgical microscope 10 contains a beam path switching device 72 with a digital mirror device 150 and a plurality of deflection mirrors 160, 162 and 164.

Figure 25:
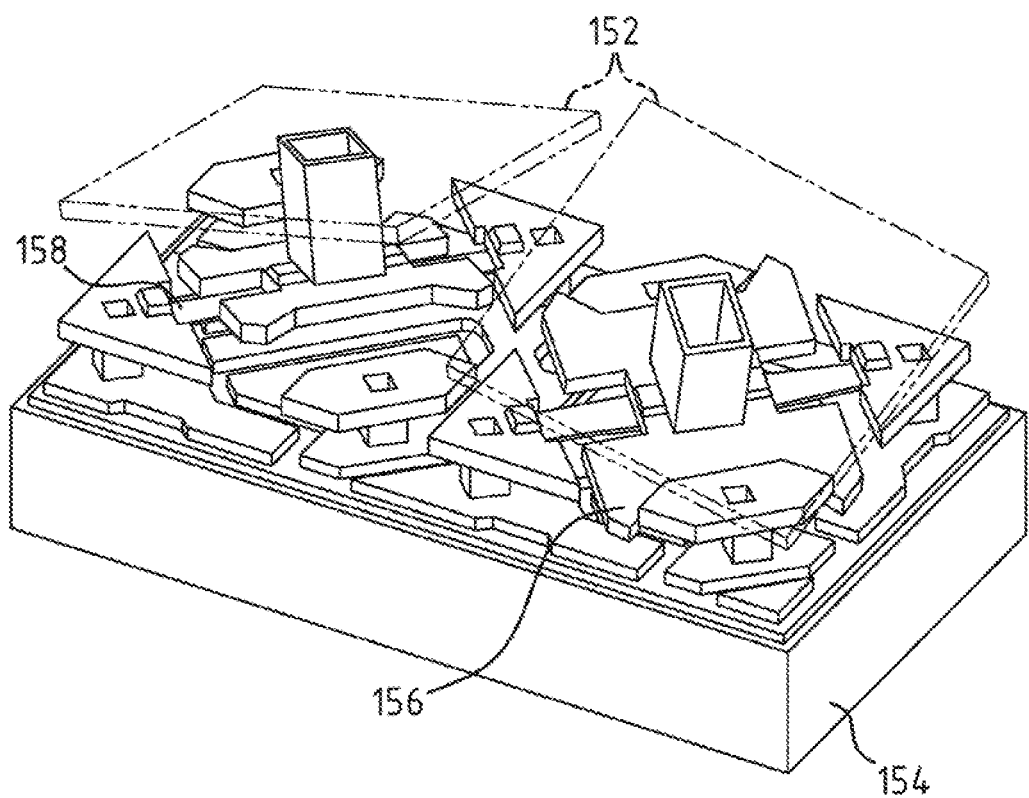
FIG. 25 shows a digital mirror display for use in the surgical microscope.

FIG. 25 is a three-dimensional partial view of the digital mirror device 150. The digital mirror device 150 contains a multiplicity of movable micromirrors 152 which are electrically adjustable by voltage being applied to adjustment electrodes 156 arranged on a carrier 154 in order to thus produce electrical power that acts counter to a torsion spring 158.

Using the micromirrors 152, the light that is guided from the object region 12 with an observation beam path in the surgical microscope 10 can be selectively guided into an eyepiece 32 or an image capturing device 40 by way of deflection mirrors 160, 162, 164. Depending on the selected setting of the micromirrors 152, only the eyepiece 32 or only the image capturing device 40 or both the eyepiece 32 and the image capturing device 40 receives the light from the object region 12.

It should be noted that the beam path switching device 72 in the previously described surgical microscope 10 can in principle also be used for coupling image information into a stereoscopic partial observation beam path.

Figure 26A:
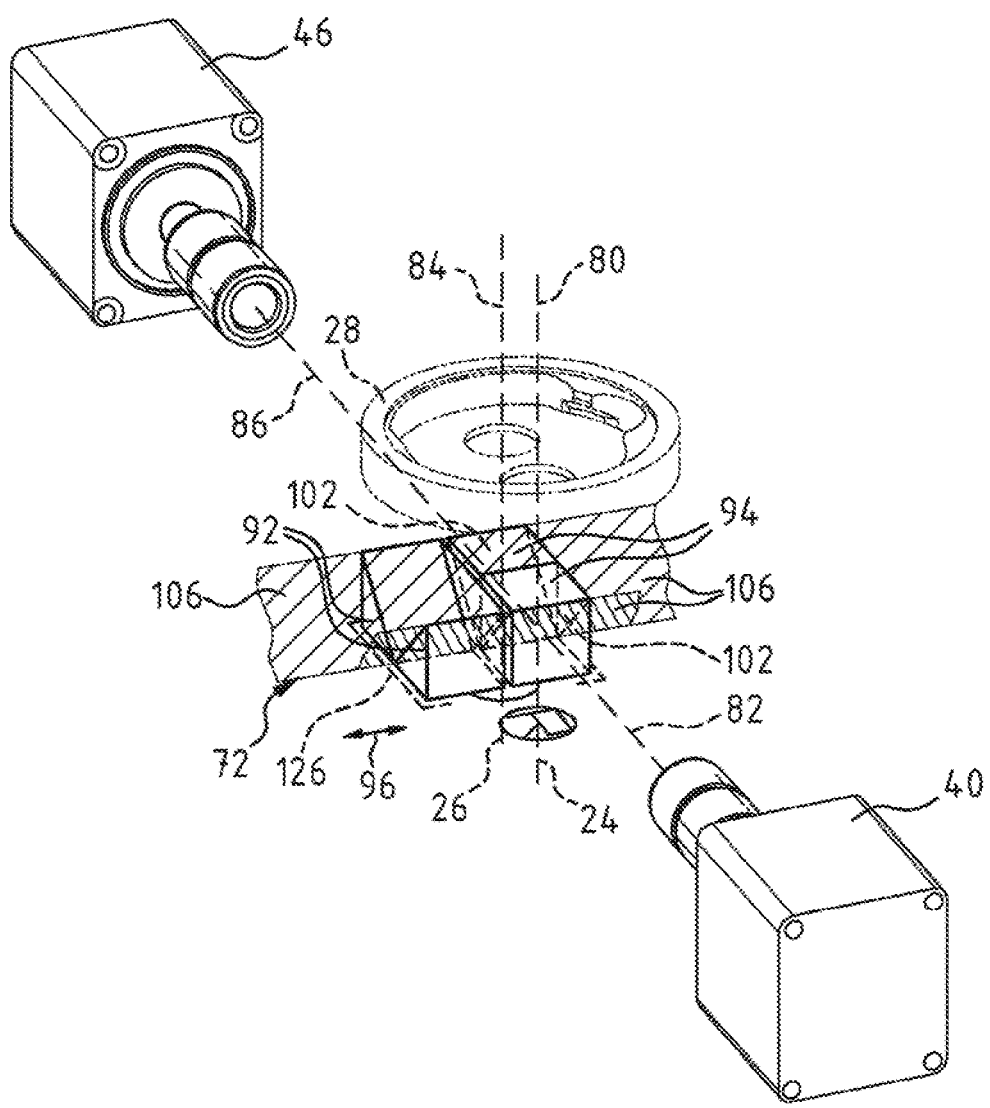
FIG. 26A and FIG. 26B show a further beam path switching device for use in a surgical microscope for stereoscopically visualizing an object region, with which two different switching states are settable.
Figure 26B:
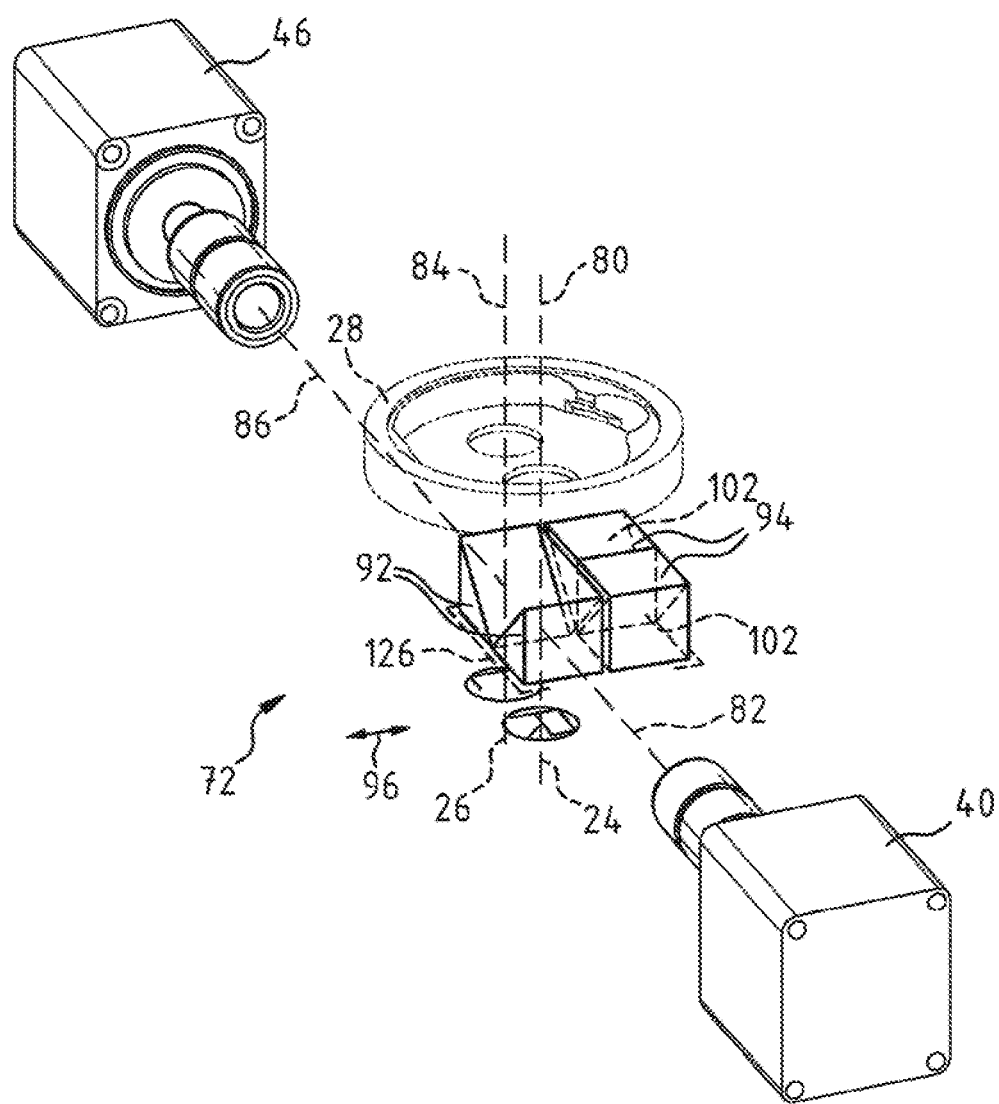

FIG. 26A and FIG. 26B show a further beam path switching device 72 in different switching states that is suitable for use in a surgical microscope that corresponds in principle to the previously described surgical microscope 10.

The beam path switching device 72 has two deflection elements 92 in the form of a deflection prism and two splitter prisms in the form of a beam splitter element 94. The deflection elements 92 and the beam splitter elements 94 are arranged on a common carrier apparatus 126 that is displaceable such that it moves linearly in the direction of the double-headed arrow 96. The deflection elements 92 in each case have a mirror face arranged in a mirror plane, the mirror face being arranged in a mirror plane 106 in which the splitter layer 102 of the deflection element 92 is located.

In the first switching state of the beam path switching device 72 shown in FIG. 26A, the beam splitter elements 94 are arranged in the manner of a large optical unit through which two stereoscopic partial observation beam paths extend at the same time in the first stereoscopic partial observation beam path 24 and in the second stereoscopic partial observation beam path 26. The light that is guided from the stereoscopic partial observation beam paths 24 and 26 to the beam splitter element 94 is split here at a splitter layer 102 in the beam splitter element 94 among the first beam path 80 and the second beam path 82, and among the further first beam path 84 and the further second beam path 86, respectively. The optical axes of the first beam path 84 and of the second beam path 86 are here located in a plane in which the optical axes of the first and second stereoscopic partial beam paths 24, 26 extend. The first beam path 84 and the second beam path 86 are guided to a first image capturing device 40 and to a second image capturing device 46, respectively.

In the second switching state of the beam path switching device 72, shown in FIG. 26B, the deflection elements 92 are arranged in the stereoscopic partial observation beam path 24 and the stereoscopic partial observation beam path 26. In this switching state, the beam splitter elements 94 are located outside the stereoscopic partial observation beam path 24 and the stereoscopic partial observation beam path 26. In the switching state shown in FIG. 26B, the beam path switching device 72 steers the light from the stereoscopic partial observation beam path 24, 26 through the beam splitter element 94 by way of the deflection elements 92.

It should be noted that the deflection element 92, in the form of a deflection prism, for deflecting the partial observation beam path 24 and the beam splitter element 94 for splitting the partial observation beam path 24 among the first beam path 80 and the second beam path 82 can be fixedly connected to one another.

Figure 26C:
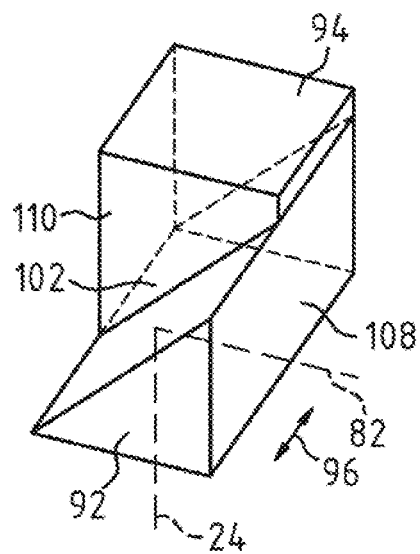
FIG. 26C and FIG. 26D show a deflection element and a beam splitter element for use in the beam path switching device, which are configured as a single-piece optical assembly.

It is possible for example that the deflection element 92 and the beam splitter element 94, as shown in FIG. 26C, are embodied as a single-piece optical assembly that has a first prism glass body 108 through which the stereoscopic partial observation beam path 24 extends both in the first and in the second switching state of the beam path switching device 72, and contains a second prism glass body 110, cemented onto the first prism glass body 108, having the splitter layer 102 through which the stereoscopic partial observation beam path 24 extends only in the second switching state of the beam path switching device 72 and which forms the beam splitter element 94 with the first prism glass body 108.

Figure 26D:
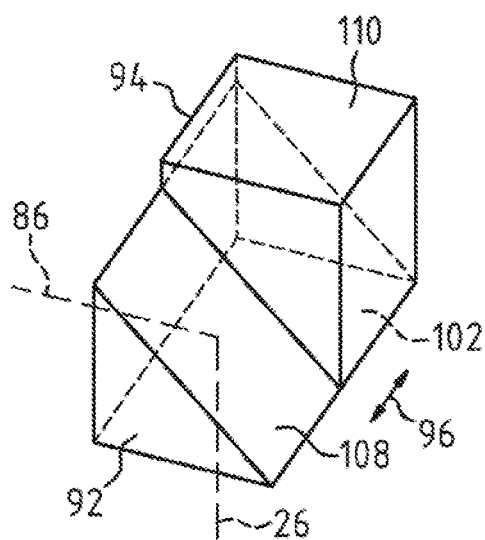

Accordingly, it is possible that the deflection element 92 and the beam splitter element 94, as shown in FIG. 26D, are embodied as a single-piece optical assembly that has a first prism glass body 108 through which the stereoscopic partial observation beam path 26 extends both in the first and in the second switching state of the beam path switching device 72, and contains a second prism glass body 110, cemented onto the first prism glass body 108, having the splitter layer 102 through which the stereoscopic partial observation beam path 26 extends only in the second switching state of the beam path switching device 72 and which forms the beam splitter element 94 with the first prism glass body 108.

Such a single-piece optical assembly described above makes precise switching of the beam paths in the surgical microscope with relatively low adjustment complexity possible. Moreover, the production of such an optical assembly does not require too great a production outlay.

Figure 27A:
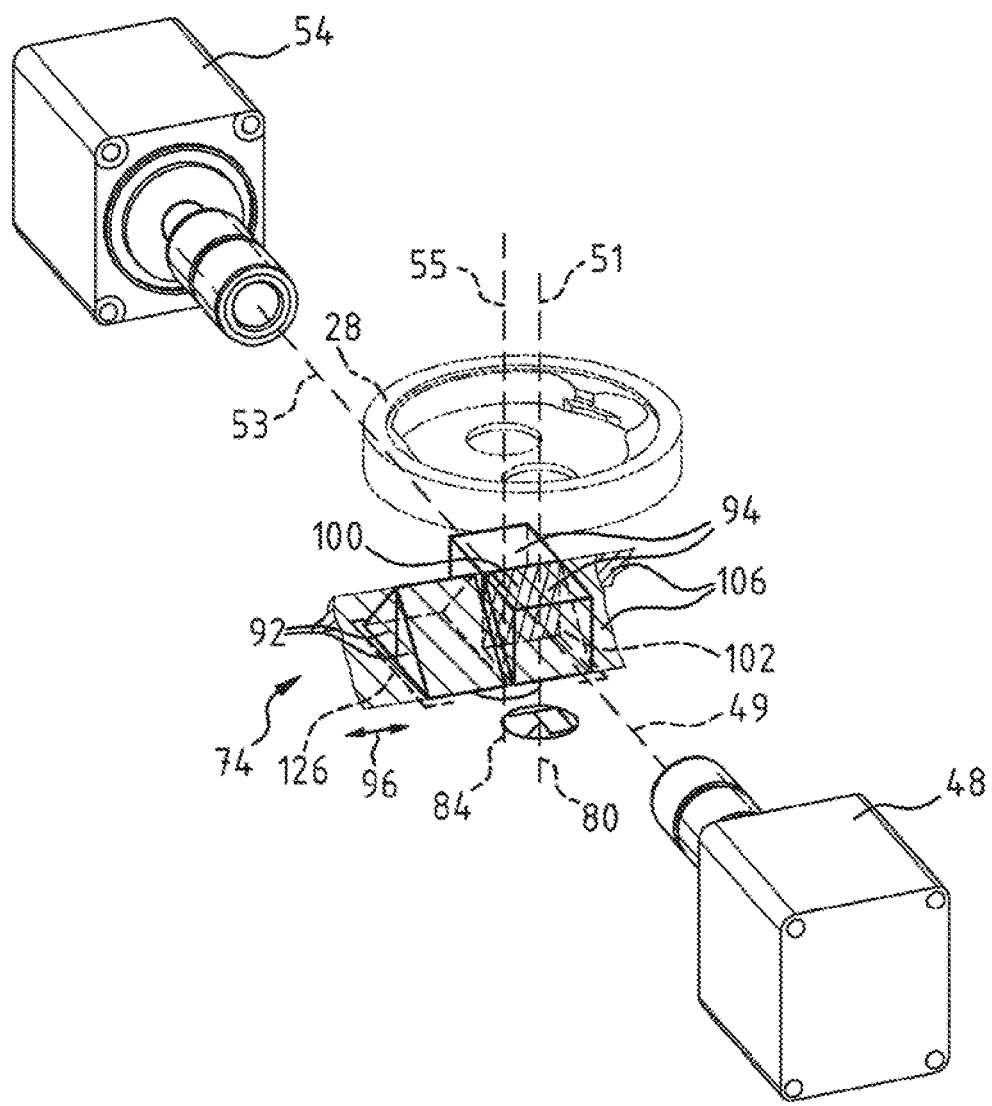
FIG. 27A and FIG. 27B show a further beam path switching device for use in a surgical microscope for stereoscopically visualizing an object region, with which two different switching states are settable; and, FIG. 27C and FIG. 27D show a deflection element and a beam splitter element for use in the beam path switching device, which are configured as a single-piece optical assembly.
Figure 27B:
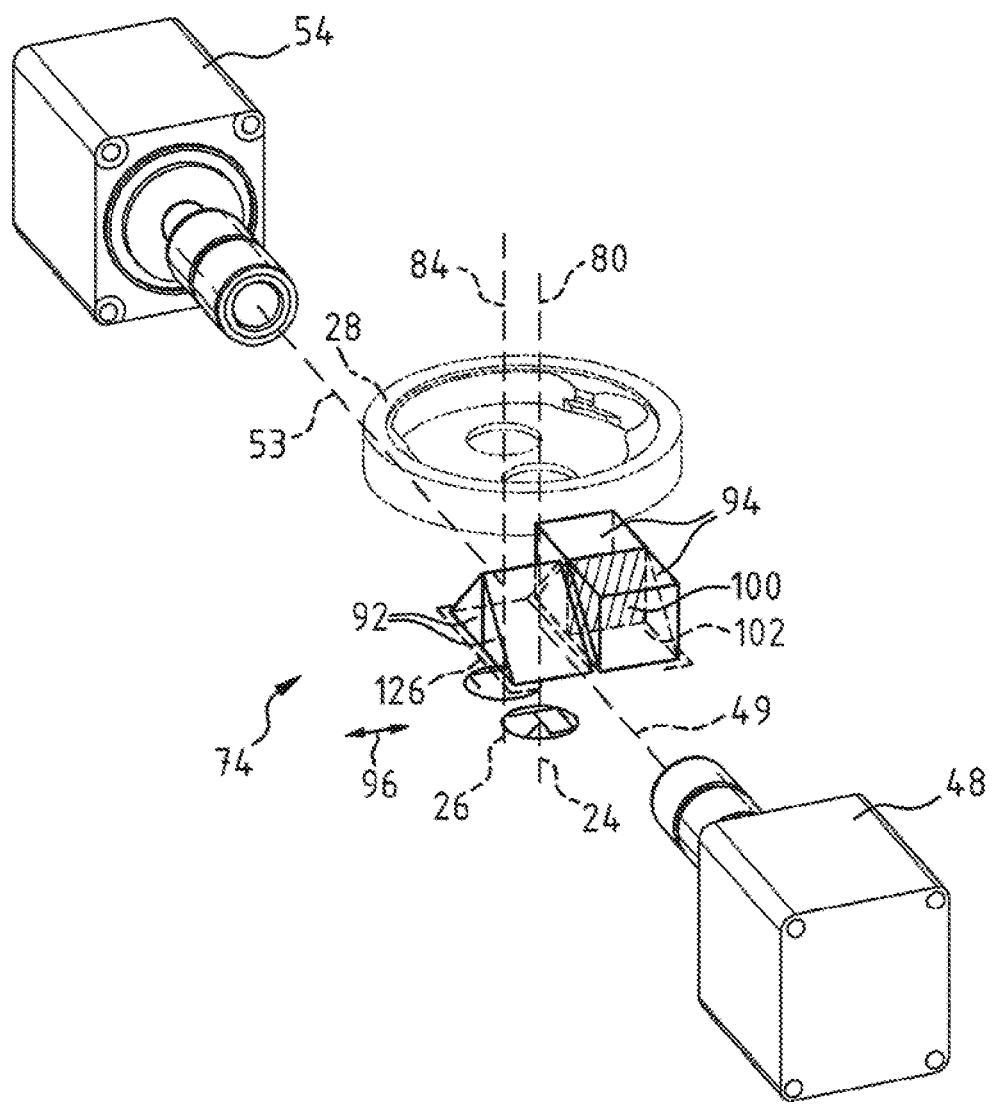

FIG. 27A and FIG. 27B show a further beam path switching device 74 with a first and a second display device 48, 54 in different switching states that is suitable for use in a surgical microscope that corresponds to the previously described surgical microscope 10. The beam path switching device 74 likewise has deflection elements 92 in the form of a deflection prism and splitter prisms in the form of a beam splitter element 94. The deflection elements 92 and the beam splitter elements 94 are arranged here, too, on a common carrier apparatus 126 that is displaceable such that it moves linearly in the direction of the double-headed arrow 96. A deflection element 92 here, too, has a mirror face that is arranged in a mirror plane 106 in which a splitter layer 102 of a beam splitter element 94 is also arranged. The two beam splitter elements 94 are separated by a light trap 100.

In the first switching state of the beam path switching device 74, shown in FIG. 27A, the beam splitter elements 94 superpose the first display beam path 49 and the second display beam path 53 on the first beam path 80 and the further first beam path 84.

The beam splitter elements 94 are here arranged in the first beam path 80 and in the further first beam path 84. The light that is guided from the beam paths 80 and 84 to the beam splitter element 94 is then split at a splitter layer 102 in the beam splitter element 94 among the first beam path 51 to the first eyepiece 32 and a further beam path to a light trap 100 and among the beam path 55 to the further eyepiece 34 and a further beam path to the light trap 100. Accordingly, the light that is guided from the display beam paths 49, 53 to the beam splitter element 94 is split at the splitter layer 102 in the beam splitter element 94 among the first beam path 51 to the first eyepiece 32 and a further beam path to the light trap 100 and among the further first beam path 55 to the further eyepiece 34 and a further beam path to the light trap 100. The optical axes of the display beam paths 49, 53 are here located in a plane in which the optical axes of the first and second stereoscopic partial beam paths 24, 26 extend.

In the second switching state shown in FIG. 27B, the beam path switching device 74 steers the light by way of the respective deflection element 92 from the display beam paths 49 and 53 into the beam path 51 to the first eyepiece 32 and the beam path 55 to the second eyepiece 34.

It should be noted that the deflection element 92, in the form of a deflection prism, for deflecting the display beam path 49 and the beam splitter element 94 for superposing the display beam path 49 with the light from the beam path 80 can be fixedly connected to one another.

Figure 27C:
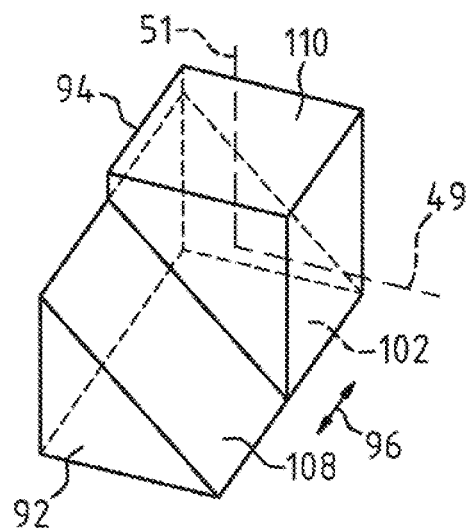

It is possible for example that the deflection element 92 and the beam splitter element 94, as shown in FIG. 27C, are embodied as a single-piece optical assembly that has a first prism glass body 108 which both in the first and in the second switching state of the beam path switching device 74 receives light guided in the display beam path 49, and contains a second prism glass body 110, cemented onto the first prism glass body 108, having the splitter layer 102 which receives light guided in the display beam path 49 only in the first switching state of the beam path switching device 74.

Figure 27D:
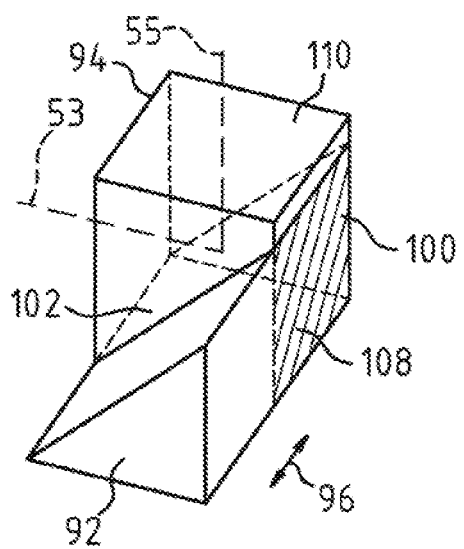

Accordingly, it is possible that the deflection element 92 and the beam splitter element 94, as shown in FIG. 27D, are embodied as a single-piece optical assembly that has a first prism glass body 108 which both in the first and in the second switching state of the beam path switching device 74 receives light guided in the display beam path 53, and contains a second prism glass body 110, cemented onto the first prism glass body 108, having the splitter layer 102 which receives light guided in the display beam path 53 only in the first switching state of the beam path switching device 74. A layer absorbing the light is applied on the prism glass body 108 in the region of the prism glass body 110 so as to thus form the light trap 100.

Such a single-piece optical assembly described above likewise makes precise switching of the beam paths in the surgical microscope with relatively low adjustment complexity possible. Moreover, the production of such an optical assembly does not require too great a production outlay.

It should be noted that the invention also extends to a surgical microscope in which combinations of features from different embodiments, described above, can be found.

To sum up, the following preferred features of the invention should be noted in particular: The invention relates to a surgical microscope 10 for producing an observation image of an object region 12 with an observation beam path 24, 26 that extends through a main objective system 16 and with a beam path switching device 72, 76 for coupling out image information that splits light that is guided in the observation beam path 24, 26 in a first switching state among a first beam path 80, 84 with light of the intensity IT1 and a second beam path 82, 86 with light of the intensity IT2. The first beam path 80, 84 is guided here to an eyepiece 32, 34 and the second beam path 82, 86 is guided to an image capturing device 40, 46. In a second switching state, the beam path switching device 72, 76 deflects the light that is guided in the observation beam path 24, 26 with the intensity IU into the second beam path 82, 86. The beam path switching device 72 has for the output coupling of image information a beam splitter element 94 that is movable into the observation beam path 24 and out of the observation beam path 24 and contains a deflection element 92 that is movable into the observation beam path 24 and out of the observation beam path 24, wherein the beam splitter element 94, when it is arranged in the observation beam path 24, splits the light that is guided therein among the first beam path 80 and the second beam path 82 and wherein the deflection element 92, when it is arranged in the observation beam path 24, deflects the light that is guided therein into the second beam path 82.

Embodiments of the invention are also reviewed in clauses 1 to 38 set forth below:

1. A surgical microscope (10) for producing an observation image of an object region (12),
   comprising an observation beam path (24, 26) that extends through a main objective system (16),
   wherein
   a beam path switching device (72, 76), arranged in the observation beam path (24, 26), for coupling out image information, is provided,
   which beam path switching device in a first switching state splits light that is guided in the observation beam path (24, 26) among a first beam path (80, 84) with light of the intensity IT1 and a second beam path (82, 86) with light of the intensity IT2, wherein the first beam path (80, 84) is guided to an eyepiece (32, 34) and the second beam path (82, 86) is guided to an image capturing device (40, 46), and
   which beam path switching device in a second switching state deflects the light that is guided in the observation beam path (24, 26) with the intensity IU into the second beam path (82, 86).

2. The surgical microscope in accordance with clause 1, wherein the beam path switching device (72, 76) in a third switching state transfers light of the intensity IB that is guided in the observation beam path (24, 26) into the first beam path (80, 84) as light of the intensity IB.

3. The surgical microscope in accordance with clause 1, wherein a beam path switching device (74, 78) for coupling in image information, which beam path switching device in a first switching state superposes image information provided on a display device (48, 54) with a beam path (49, 53) onto the first beam path (80, 84) and which beam path switching device in a second switching state supplies the image information provided on the display device (48, 54) with the beam path (49, 53) to the eyepiece (32, 34) without light from the first beam path (80, 84).

4. The surgical microscope in accordance with clause 2, wherein a beam path switching device (74, 78) for coupling in image information, which beam path switching device in a first switching state superposes image information provided on a display device (48, 54) with a beam path (49, 53) onto the first beam path (80, 84) and which beam path switching device in a second switching state supplies the image information provided on the display device (48, 54) with the beam path (49, 53) to the eyepiece (32, 34) without light from the first beam path (80, 84).

5. The surgical microscope in accordance with clause 3, wherein a coupling device (88) which couples the beam path switching device (72, 76) for the output coupling of image information and couples the beam path switching device (74, 78) for the input coupling of image information for setting switching states that are coordinated with one another such that,
   when setting the first switching state of the beam path switching device (72, 76) for the output coupling of image information, the first switching state of the beam path switching device (74, 78) for the input coupling of image information is set, or when setting the first switching state of the beam path switching device (74, 78) for the input coupling of image information, the first switching state of the beam path switching device (72, 76) for the output coupling of image information is set, and
   when setting the second switching state of the beam path switching device (72, 76) for the output coupling of image information, the second switching state of the beam path switching device (74, 78) for the input coupling of image information is set, or when setting the second switching state of the beam path switching device (74, 78) for the input coupling of image information, the second switching state of the beam path switching device (72, 76) for the output coupling of image information is set.

6. The surgical microscope in accordance with clause 4, wherein a coupling device (88) which couples the beam path switching device (72, 76) for the output coupling of image information and couples the beam path switching device (74, 78) for the input coupling of image information for setting switching states that are coordinated with one another such that,
   when setting the first switching state or the third switching state of the beam path switching device (72, 76) for the output coupling of image information, the first switching state of the beam path switching device (74, 78) for the input coupling of image information is set, or when setting the first switching state of the beam path switching device (74, 78) for the input coupling of image information, the first switching state or the third switching state of the beam path switching device (72, 76) for the output coupling of image information is set, and
   when setting the second switching state of the beam path switching device (72, 76) for the output coupling of image information, the second switching state of the beam path switching device (74, 78) for the input coupling of image information is set, or when setting the second switching state of the beam path switching device (74, 78) for the input coupling of image information, the second switching state of the beam path switching device (72, 76) for the output coupling of image information is set.

7. The surgical microscope in accordance with clause 3, wherein in a third switching state the beam path switching device (74, 78) for the input coupling of image information guides light that is guided in the first beam path (80, 84) without light from the beam path (49, 53) from the display device (48, 54) to the eyepiece (32, 34).

8. The surgical microscope in accordance with clause 4, wherein in the third switching state the beam path switching device (74, 78) for the input coupling of image information guides light that is guided in the first beam path (80, 84) without light from the beam path (49, 53) from the display device (48, 54) to the eyepiece (32, 34).

9. The surgical microscope in accordance with clause 7, wherein a coupling device (88) which couples the beam path switching device (72, 76) for the output coupling of image information and couples the beam path switching device (74, 78) for the input coupling of image information for setting switching states that are coordinated with one another such that,
   when setting the first switching state of the beam path switching device (72, 76) for the output coupling of image information, the first switching state or third switching state of the beam path switching device (74, 78) for the input coupling of image information is set, or when setting the first switching state or third switching state of the beam path switching device (74, 78) for the input coupling of image information, the first switching state of the beam path switching device (72, 76) for the output coupling of image information is set, and
   when setting the second switching state of the beam path switching device (72, 76) for the output coupling of image information, the second switching state of the beam path switching device (74, 78) for the input coupling of image information is set, or when setting the second switching state of the beam path switching device (74, 78) for the input coupling of image information, the second switching state of the beam path switching device (72, 76) for the output coupling of image information is set.

10. The surgical microscope in accordance with clause 8, wherein a coupling device (88) which couples the beam path switching device (72, 76) for the output coupling of image information and couples the beam path switching device (74, 78) for the input coupling of image information for setting switching states that are coordinated with one another such that,
    when setting the first switching state or the third switching state of the beam path switching device (72, 76) for the output coupling of image information, the first switching state or third switching state of the beam path switching device (74, 78) for the input coupling of image information is set, or when setting the first switching state or third switching state of the beam path switching device (74, 78) for the input coupling of image information, the first switching state or the third switching state of the beam path switching device (72, 76) for the output coupling of image information is set, and
    when setting the second switching state of the beam path switching device (72, 76) for the output coupling of image information, the second switching state of the beam path switching device (74, 78) for the input coupling of image information is set, or when setting the second switching state of the beam path switching device (74, 78) for the input coupling of image information, the second switching state of the beam path switching device (72, 76) for the output coupling of image information is set.

11. The surgical microscope in accordance with one of clauses 1 to 10, wherein the beam path switching device (72) has for the output coupling of image information a beam splitter element (94) that is movable into the observation beam path (24) and out of the observation beam path (24) and contains a deflection element (92) that is movable into the observation beam path (24) and out of the observation beam path (24), wherein the beam splitter element (94), when it is arranged in the observation beam path (24), splits the light that is guided therein among the first beam path (80) and the second beam path (82) and wherein the deflection element (92), when it is arranged in the observation beam path (24), deflects the light that is guided therein into the second beam path (82).

12. The surgical microscope in accordance with clause 11, wherein the observation beam path (24) that was deflected into the second beam path (82) by the deflection element (92) upon the arrangement thereof in the observation beam path (24) extends through the beam splitter element (94).

13. The surgical microscope in accordance with clause 12, wherein a light trap (100) for receiving light that is coupled out of the second beam path (82) using the beam splitter element (94) when the deflection element (92) is arranged in the observation beam path (24).

14. The surgical microscope in accordance with one of clauses 11 to 13, wherein the beam splitter element (94) and the deflection element (92) are secured on a common carrier element (98).

15. The surgical microscope in accordance with clause 14, wherein the carrier element (98) is displaceable so as to move linearly for moving the beam splitter element (94) and the deflection element (92) into and out of the observation beam path (24) in a plane through which the observation beam path (24) extends, in particular in a plane that is perpendicular to the observation beam path (24).

16. The surgical microscope in accordance with one of clauses 11 to 13, wherein the beam splitter element (94) and the deflection element (92) are arranged to be displaceable in relation to one another.

17. The surgical microscope in accordance with one of clauses 11 to 16, wherein it is possible to set, for the beam path switching device (72) for the output coupling of image information, a setting in which both the deflection element (92) and the beam splitter element (94) are arranged outside the observation beam path (24).

18. The surgical microscope in accordance with one of clauses 1 to 10, wherein the beam path switching device (72) contains a beam splitter element, arranged in the observation beam path (24), having an electrically settable splitter layer (102) that, in a first setting, splits the light that is guided in the observation beam path (24) among the first beam path (80) and the second beam path (82) and that, in a second setting, deflects the light that is guided in the observation beam path (24) into the second beam path (82).

19. The surgical microscope in accordance with clause 18, wherein, in a third setting, the splitter layer (102) releases the light that is guided in the observation beam path (24).

20. The surgical microscope in accordance with clause 11, wherein the beam splitter element (94) and the deflection element (92) are rotatable about an axis of rotation (118) that is parallel or skewed with respect to an optical axis of the observation beam path (24) for moving into and out of the observation beam path (24).

21. The surgical microscope in accordance with clause 11, wherein the beam splitter element (94) and the deflection element (92) are rotatable about an axis of rotation (118) that is located in a plane perpendicular with respect to the observation beam path (24) for moving into and out of the observation beam path (24).

22. The surgical microscope in accordance with one of clauses 1 to 10, wherein the beam path switching device (72) contains for the output coupling of image information a beam splitter element (94), which is rotatable in the observation beam path (24) about an axis of rotation (118) that is located in a plane perpendicular to the observation beam path (24), with a splitter layer (102) and a deflection element (92), configured as a plane mirror and rotatable in the observation beam path (24) about an axis of rotation (120) that is located in a plane perpendicular to the observation beam path (24), wherein, in a first setting of the beam path switching device (72), the beam splitter element (94) splits the light that is guided in the observation beam path (24) among the first beam path (80) and the second beam path (82) by way of the splitter layer (102), wherein, in a second setting, the beam path switching device (72) deflects the light that is guided in the observation beam path (24) into the second beam path (82) by way of the deflection element (92), and wherein, in a third setting, the beam path switching device (72) releases the light that is guided in the observation beam path (24) into the first beam path (80).

23. The surgical microscope in accordance with one of clauses 1 to 10, wherein the beam path switching device (72) contains for the output coupling of image information a digital mirror device (150) arranged in the observation beam path (24).

24. The surgical microscope in accordance with one of clauses 3 to 10, wherein the beam path switching device (74) has for the input coupling of image information a beam splitter element (94) that is movable into the first beam path (80) and out of the first beam path (80) and contains a deflection element (92) that is movable into the first beam path (80) and out of the first beam path (80), wherein the beam splitter element (94), when it is arranged in the first beam path (80), superposes the image information that is provided on the display device (48) with the beam path (49) on the first beam path (80) and wherein the deflection element (92), when it is arranged in the first beam path (80), deflects the beam path (49) with the image information provided on the display device (48) to the eyepiece (32).

25. The surgical microscope in accordance with clause 24, wherein the beam path (49) that was deflected by the deflection element (92), upon arrangement in the first beam path (80) to the eyepiece (32) with the image that is provided on the display device (48) extends through the beam splitter element (94).

26. The surgical microscope in accordance with either of clauses 24 and 25, wherein at least one light trap (100) for receiving light that is deflected out of the beam path (49) with the image that is provided on the display device (48) by way of the beam splitter element (94) upon arrangement of the deflection element (92) in the first beam path (80).

27. The surgical microscope in accordance with one of clauses 24 to 26, wherein the beam splitter element (94) and the deflection element (92) are secured on a common carrier (98).
28. The surgical microscope in accordance with clause 27, wherein the carrier element (98) is displaceable so as to move linearly for moving the beam splitter element (94) and the deflection element (92) into and out of the first beam path (80) in a plane through which the first beam path (80) extends, in particular in a plane that is perpendicular to the first beam path (80).
29. The surgical microscope in accordance with one of clauses 24 to 26, wherein the beam splitter element (94) and the deflection element (92) are arranged to be displaceable in relation to one another.
30. The surgical microscope in accordance with one of clauses 24 to 29, wherein it is possible to set, for the beam path switching device (74) for the input coupling of image information, a setting in which both the deflection element (92) and the beam splitter element (94) are arranged outside the first beam path (80).
31. The surgical microscope in accordance with one of clauses 3 to 10, wherein the beam path switching device (74) contains a beam splitter element, arranged in the first beam path (80), having an electrically settable splitter layer (102) that, in a first setting, superposes the beam path (49) with the image that is provided on the display device (48) on the first beam path (80) and, in a second setting, deflects the beam path (49) with the image that is provided on the display device (48) to the eyepiece (32).
32. The surgical microscope in accordance with clause 31, wherein, in a third setting, the splitter layer (102) releases the light that is guided in the first beam path (80).
33. The surgical microscope in accordance with one of clauses 24, 26, 27, 29 and 30, wherein the beam splitter element (94) and the deflection element (92) are rotatable about an axis of rotation (118) that is parallel or skewed with respect to an optical axis of the first beam path (80) for moving into and out of the first beam path (80).
34. The surgical microscope in accordance with one of clauses 24, 26, 27, 29 and 30, wherein the beam splitter element (94) and the deflection element (92) are rotatable about an axis of rotation (118) that is located in a plane perpendicular to the first beam path (80) for moving into and out of the first beam path (80).
35. The surgical microscope in accordance with one of clauses 3 to 10, wherein the beam path switching device (74) contains for the input coupling of image information a beam splitter element (94), which is rotatable into the first beam path (80) about an axis of rotation (118) that is located in a plane perpendicular to the first beam path (80), with a splitter layer (102) and a plane mirror (92) that is rotatable in the first beam path (80) about an axis of rotation (120) that is located in a plane perpendicular to the first beam path (80), wherein, in a first setting of the beam path switching device (74), the beam splitter element (94) superposes the beam path (49) with the image information that is provided on the display device (48) on the first beam path (80) by way of the splitter layer (102), wherein, in a second setting, the beam path switching device (74) deflects the beam path (49) with the image information that is provided on the display device (48) into the beam path (51) to the first eyepiece (32) by way of the plane mirror (92), and wherein, in a third setting, the beam path switching device (74) releases the first beam path (80).
36. The surgical microscope in accordance with clause 35, wherein the beam path switching device (74) contains a light trap (100) for receiving light from the beam path (49) that extends through the rotatable beam splitter element (94) in the first setting of the beam path switching device (74).
37. The surgical microscope in accordance with one of clauses 3 to 10, wherein the beam path switching device (74) contains for the input coupling of image information a digital mirror device (150) arranged in the first beam path (80).
38. The surgical microscope in accordance with one of clauses 1 to 37, wherein the observation beam path that extends through the main objective system (16) is a first stereoscopic partial observation beam path (24) or a second stereoscopic partial observation beam path (26).

It is understood that the foregoing description is that of the preferred embodiments of the invention and that various changes and modifications may be made thereto without departing from the spirit and scope of the invention as defined in the appended claims.

LIST OF REFERENCE SIGNS

10 Surgical microscope
12 Object region
14 Imaging optical unit
16 Main microscope objective system
18 Main body
20 Illumination device
22 Afocal magnification system
24 First stereoscopic partial viewing or observation beam path
26 Second stereoscopic partial viewing or observation beam path
28 Interface
30 Binocular tube
32 First eyepiece
34 Second eyepiece
36 Right eye
38 Left eye
40 First image capturing device
42 Objective lens system
44 Image sensor
46 Second image capturing device
48 First display device
49, 49', 49" First display beam path
50 Display
51, 51', 51" Beam path
52 Display lens
53, 53' Second display beam path
54 Second display device
55, 55' Beam path
56 Tube lens
58 Intermediate image plane
60 Image processing and control device
62 Computational unit
64, 66, 68 Coordinate system
70 Image reproducing device
72, 72', 74, 76, 78 Beam path switching device
80 First beam path
82 Second beam path
84 Further first beam path
86 Further second beam path
87 Control device
88 Coupling device
90 Input unit 92 Deflection element
94 Beam splitter element
96 Double-headed arrow
98, 99 Carrier element
100 Light trap
102 Splitter layer
104, 104' Beam paths
106 Mirror plane
108, 110 Prism glass body
117 Double-headed arrow
118 Axis of rotation
119 Double-headed arrow
120 Axis of rotation
126 Carrier apparatus
132 Passage-opening
136 Cutout
142 Carrier apparatus
150 Digital Mirror Device
152 Micromirror
153 Observation beam path
154 Carrier
156 Adjustment electrode
158 Torsion spring
160, 162, 164 Deflection mirror

What is claimed is:

1. A surgical microscope for generating an observation image of an object region, the surgical microscope comprising:
an eyepiece;
a main objective system;
said eyepiece and said main objective system conjointly defining a viewing beam path extending through said main objective system toward said object region;
an image capturing device;
a beam path switching device arranged in said viewing beam path for out-coupling image information;
said beam path switching device being switchable between a first switching state wherein light conducted in said viewing beam path is split into a first component along a first beam path to said eyepiece at an intensity IT1 and a second component along a second beam path to said image capturing device at an intensity IT2 and a second switching state wherein said light conducted in said viewing beam path is deflected only into said second beam path to said image capturing device at an intensity IU;
said beam path switching device including a beam splitter movable into said viewing beam path for a first switching state and out of said viewing beam path to a location along said second beam path between said viewing beam path and said image capturing device for said second switching state;
said beam path switching device further including a deflection element movable into and out of said viewing beam path so as to permit at most one of said beam splitter and said deflection element to be in said viewing beam path at a time;
said beam splitter, in said viewing beam path, splitting said light conducted in said viewing beam path into said first and second components along said first and second beam paths, respectively, in correspondence to said first switching state;
said deflection element, in said viewing beam path, deflecting said light conducted in said viewing beam path only along said second beam path through said beam splitter to said image capturing device in correspondence to said second switching state;
said beam path switching device being configured to position said beam splitter into said second beam path in said second switching state; and,
said surgical microscope further comprising a light trap for receiving light coupled out of said second beam path via said beam splitter with said deflection element arranged in said viewing beam path in correspondence to said second switching state.

2. The surgical microscope of claim 1 further comprising a carrier common to both said beam splitter and said deflection element; and, said beam splitter and said deflection element being secured on said common carrier.

3. The surgical microscope of claim 2, wherein said common carrier is displaceable so as to move linearly for moving said beam splitter and said deflection element into and out of said viewing beam path in a plane through which said viewing beam path extends.

4. The surgical microscope of claim 3, wherein said plane is perpendicular to said viewing beam path.

5. The surgical microscope of claim 1, wherein said beam path switching device for said out-coupling of said image information is configured to permit an adjustment thereof to a setting wherein both said deflection element and said beam splitter are arranged outside said viewing beam path.

6. The surgical microscope of claim 1, wherein said beam path switching device is switchable into a third switching state wherein said beam splitter and said deflection element are out of said viewing beam path so as to permit light of an intensity IB, which is guided in the viewing beam path, to be transferred into the first beam path as light of said intensity IB.

7. The surgical microscope of claim 6, wherein said beam path switching device is a first beam path switching device; and, said surgical microscope further comprises:
a display device for displaying image information;
a second beam path switching device for in-coupling image information;
said second beam path switching device being switchable between a first switching state wherein said second beam path switching device superposes image information from said display device via a third beam path onto said first beam path and a second switching state wherein said second beam path switching device supplies said image information from said display device via said third beam path to said eyepiece without light from said first beam path.

8. The surgical microscope of claim 7, further comprising:
a coupling unit for coupling said first beam path switching device and said second beam path switching device to set mutually matched switching states wherein:
a setting of said first switching state or said third switching state of said first beam path switching device causes a setting into said first switching state of said second beam path switching device, or a setting of said first switching state of said second beam path switching device causes a setting into said first switching state or said third switching state of said first beam path switching device; and,
a setting of said second switching state of said first beam path switching device causes a setting into said second switching state of said second beam path switching device, or a setting of said second switching state of said second beam path switching device causes a setting into said second switching state of said first beam path switching device.

9. The surgical microscope of claim 7, wherein said second beam path switching device is switchable into a third switching state wherein said second beam path switching device conducts light guided in said first beam path to said eyepiece without light from said third beam path from said display device.

10. The surgical microscope of claim 9, further comprising:
a coupling unit for coupling said first beam path switching device and said second beam path switching device to set mutually matched switching states wherein:
a setting of said first switching state or said third switching state of said first beam path switching device for the out-coupling of image information causes a setting into said first switching state or said third switching state of said second beam path switching device for the in-coupling of image information, or a setting of said first switching state or said third switching state of said second beam path switching device for the in-coupling of image information causes a setting into said first switching state or said third switching state of said first beam path switching device for the out-coupling of image information; and,
a setting of said second switching state of said first beam path switching device for the out-coupling of image information causes a setting into said second switching state of said second beam path switching device for the in-coupling of image information, or a setting of the second switching state of said second beam path switching device for the in-coupling of image information causes a setting into said second switching state of said first beam path switching device for the out-coupling of image information.

11. The surgical microscope of claim 1, wherein said beam path switching device is a first beam path switching device; and, said surgical microscope further comprises:
a display device for displaying image information;
a second beam path switching device for in-coupling image information; and,
said second beam path switching device being switchable between a first switching state wherein said second beam path switching device superposes image information from said display device via a third beam path onto said first beam path and a second switching state wherein said second beam path switching device supplies said image information from said display device via said third beam path to said eyepiece without light from said first beam path.

12. The surgical microscope of claim 11, further comprising:
a coupling unit for coupling said first beam path switching device and said second beam path switching device to set mutually matched switching states wherein:
a setting of said first switching state of said first beam path switching device causes a setting into said first switching state of said second beam path switching device, or a setting of said first switching state of said second beam path switching device causes a setting into said first switching state of said first beam path switching device; and,
a setting of said second switching state of said first beam path switching device causes a setting into said second switching state of said second beam path switching device, or a setting of said second switching state of said second beam path switching device causes a setting into said second switching state of said first beam path switching device.

13. The surgical microscope of claim 11, wherein said second beam path switching device is switchable into a third switching state wherein said second beam path switching device conducts light guided in said first beam path to said eyepiece without light from said third beam path from said display device.

14. The surgical microscope of claim 13, further comprising:
a coupling unit for coupling said first beam path switching device and said second beam path switching device to set mutually matched switching states wherein:
a setting of said first switching state of said first beam path switching device for the out-coupling of image information causes a setting into the first switching state or third switching state of said second beam path switching device for in-coupling of image information, or a setting of the first switching state or third switching state of said second beam path switching device for the in-coupling of image information causes a setting into said first switching state of said first beam path switching device for the out-coupling of image information; and,
a setting of the second switching state of said first beam path switching device for the out-coupling of image information causes a setting into said second switching state of said second beam path switching device for the in-coupling of image information, or a setting of said second switching state of said second beam path switching device for the in-coupling of image information causes a setting into said second switching state of said first beam path switching device for the out-coupling of image information.

15. The surgical microscope of claim 11, wherein said second beam path switching device has a second beam splitter movable into said first beam path and out of said first beam path and includes a second deflection element movable into said first beam path and out of said first beam path so as to permit at most one of said second beam splitter and said second deflection element to be in said first beam path at a time; and, wherein said second beam splitter, in said first beam path, superposes the image information provided on said display device via said third beam path on said first beam path; and, wherein said second deflection element, in the first beam path, deflects said third beam path with said image information provided on said display device to said eyepiece.

16. The surgical microscope of claim 15, wherein said third beam path, which was deflected by said second deflection element, when arranged in said first beam path to said eyepiece with said image provided on said display device extends through said second beam splitter.

17. The surgical microscope of claim 15, further comprising:
at least one light trap for receiving light deflected out of said third beam path with the image that is provided on said display device via said second beam splitter upon arrangement of said second deflection element in said first beam path.

18. The surgical microscope of claim 15, wherein said second beam splitter and said second deflection element are secured on a common carrier.

19. The surgical microscope of claim 18, wherein said common carrier is displaceable so as to move linearly for moving said second beam splitter and said second deflection element into and out of said first beam path in a plane through which said first beam path extends.

20. The surgical microscope of claim 19, wherein said plane through which said first beam path extends is perpendicular to said first beam path.

21. The surgical microscope of claim 15, wherein, for said second beam path switching device for in-coupling of image information, a setting can be set wherein both said second deflection element and said second beam splitter are arranged outside the first beam path.

22. The surgical microscope of claim 1, wherein said viewing beam path that extends through said main objective system is a first stereoscopic partial viewing beam path or a second stereoscopic partial viewing beam path.

* * * * *